US009447127B2

(12) United States Patent
Notter et al.

(10) Patent No.: US 9,447,127 B2
(45) Date of Patent: *Sep. 20, 2016

(54) SYNTHETIC LUNG SURFACTANT AND USE THEREOF

(71) Applicants: University of Rochester, Rochester, NY (US); University of Guelph, Guelph (CA); The Los Angeles Biomedical Research Institute at Harbor-UCLA Medical Center, Torrance, CA (US)

(72) Inventors: Robert H. Notter, Pittsford, NY (US); Zhengdong Wang, Rochester, NY (US); Adrian L. Schwan, Guelph (CA); Zhongyi Wang, Guelph (CA); Jason A. Davy, Guelph (CA); Alan J Waring, Irvine, CA (US); Frans Walther, Renondo Beach, CA (US); Larry M. Gordon, Torrance, CA (US)

(73) Assignees: University of Rochester, Rochester, NY (US); The Los Angeles Biomedical Research Institute of Harbor-UCLA Medical Center, Torrance, CA (US); University of Guelph, Guelph, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/030,719

(22) Filed: Sep. 18, 2013

(65) Prior Publication Data
US 2014/0044775 A1 Feb. 13, 2014

Related U.S. Application Data

(62) Division of application No. 12/374,458, filed as application No. PCT/US2007/073970 on Jul. 20, 2007, now Pat. No. 8,563,683.

(60) Provisional application No. 60/807,933, filed on Jul. 20, 2006.

(51) Int. Cl.
| A61K 38/00 | (2006.01) |
| C07F 9/09 | (2006.01) |
| A61K 9/00 | (2006.01) |
| C07F 9/40 | (2006.01) |
| C07K 14/00 | (2006.01) |
| C07K 14/785 | (2006.01) |

(52) U.S. Cl.
CPC ............. *C07F 9/091* (2013.01); *A61K 9/0082* (2013.01); *C07F 9/4006* (2013.01); *C07F 9/4075* (2013.01); *C07K 14/001* (2013.01); *C07K 14/785* (2013.01)

(58) Field of Classification Search
CPC .............................. A61K 38/00; A61K 39/00
See application file for complete search history.

(56) References Cited

U.S. PATENT DOCUMENTS

| 5,262,405 A | 11/1993 | Girod-Vaquez et al. |
| 7,538,090 B1 | 5/2009 | Waring et al. |
| 8,563,683 B2 * | 10/2013 | Notter et al. ................. 530/300 |
| 2003/0040468 A1 | 2/2003 | Barron et al. |
| 2004/0037781 A1 | 2/2004 | McCormack, Jr. |
| 2004/0132967 A1 | 7/2004 | Walther et al. |

FOREIGN PATENT DOCUMENTS

| EP | 1481665 A1 | 1/2004 |
| FR | 2658418 A1 | 2/1990 |
| JP | 59181216 | 10/1984 |
| WO | 00/27360 A1 | 5/2000 |
| WO | 0047623 A1 | 8/2000 |
| WO | 01/60837 A2 | 8/2001 |
| WO | 2008044109 A1 | 4/2008 |

OTHER PUBLICATIONS

Mahendra Kumar Jain et al. (Biochimica et Biophysica Acta, Biomembranes (1986),860(3), 462-74).*
Cho et al. vol. 277, No. 26, Issue of Jun. 28, pp. 23838-23846, 2002.*
Waring et al., "The Role of Charged Amphipathic Helices in the Structure and Function of Surfactant Protein B," J. Pep. Res. 66(6):364-374 (2005).
CAPLUS Abstract 1987:549661 CEVC, "How Membrane Chain Melting Properties are Regulated by the Polar Surface of the Lipid Bilayer," Biochemistry 26(20):6305-6310 (1987).
Chang et al., "Surface Properties of Sulfur- and Ether-linked Phosphonolipids with and without Purified Hydrophobic Lung Surfactant Proteins," Chemistry and Physics of Lipids 137:77-93 (2005).
Chang et al., "Synthesis and Interfacial Behavior of Sulfur-containing Analogs of Lung Surfactant Dipalmitoyl Phosphatidylcholine," Bioorganic & Medicinal Chemistry Letters 14:5983-5986 (2004).
Wang et al., "Surface Activity of a Synthetic Lung Surfactant Containing a Phospholipase-resistant Phosphonolipid Analog of Dipalmitoyl Phosphatidylcholine," Am. J. Physiol. Lung. Mol. Physiol. 285:L550-L559 (2003).
Walther et al., "Surfactant Protein B and C Analogues," Molecular Genetics and Metabolism 71(1-2):342-351 (2000).
Walther et al., "Hydrophobic Surfactant Proteins and Their Analogues," Neonatology 91:303-310 (2007).

(Continued)

*Primary Examiner* — Marcela M Cordero Garcia
(74) *Attorney, Agent, or Firm* — LeClairRyan, a Professional Corporation

(57) ABSTRACT

The present invention relates to synthetic lung surfactant compositions that contain one or more of phospholipase-resistant phospho-glycerol derivatives, phospholipase-resistant phospho-choline derivatives, and surface active proteins or peptides, more preferably a combination of at least two or all three of these materials. Novel phospholipase-resistant phospho-glycerol derivatives, phospholipase-resistant phospho-choline derivatives, and surface active peptides are also disclosed herein. Uses of the surfactant compositions of the present invention to treat endogenous surfactant dysfunctional or deficient lung tissue, to prepare synthetic peptides for use in the surfactant compositions, and to deliver therapeutic agents are also disclosed.

27 Claims, 6 Drawing Sheets

(56) References Cited

OTHER PUBLICATIONS

Palmblad et al., "Biophysical Activity of an Artificial Surfactant Containing an Analogue of Surfactant Protein (SP)-C and Native SP-B," Biochem. J. 339:381-386 (1999).

Notter et al., "Novel Phospholipase-Resistant Lipid/Peptide Synthetic Lung Surfactants," Mini-Reviews Medicinal Chemistry 7(9):932-945 (2007).

Notter et al. "Synthesis and Surface Activity of Diether-Linked Phosphoglycerols: Potential Applications for Exogenous Lung Surfactants," Bioorg. Med. Chem. Lett. 17:113-117 (2007).

Schwan et al., "Synthesis and Activity of a Novel Diether Phosphonoglycerol in Phospholipase-Resistant Synthetic Lipid: Peptide Lung Surfactants," Med. Chem. Commun. doi 10.1039/c1md00206f (2011).

Walther et al., "Dynamic Surface Activity of a Fully Synthetic Phospholipase-Resistant Lipid/Peptide Lung Surfactant," PLoS One 10(e1039):1-10 (2007).

* cited by examiner

Figure 13
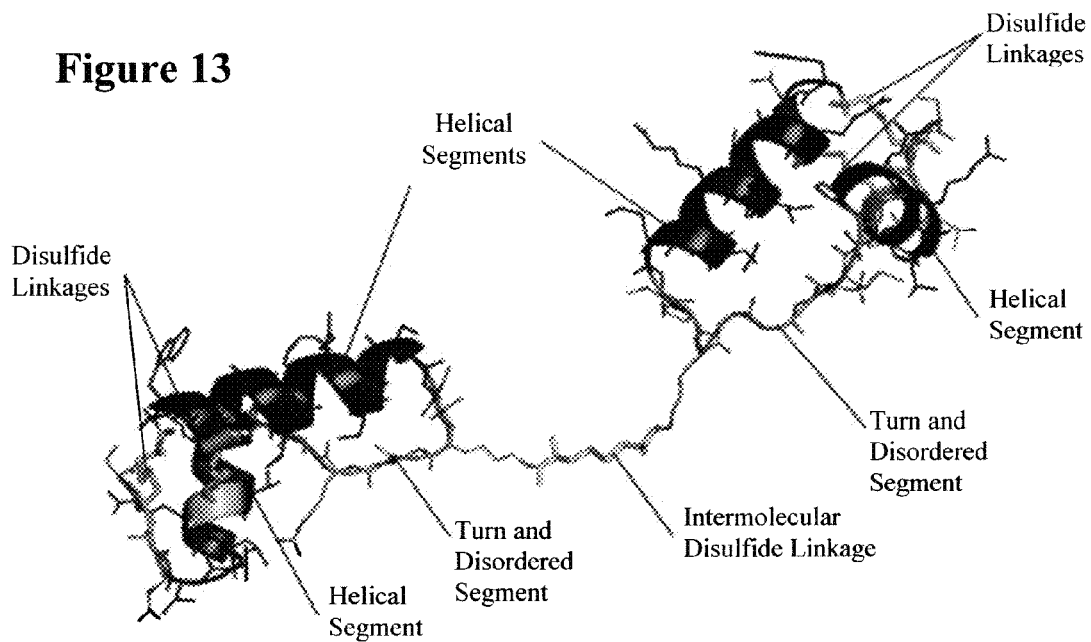
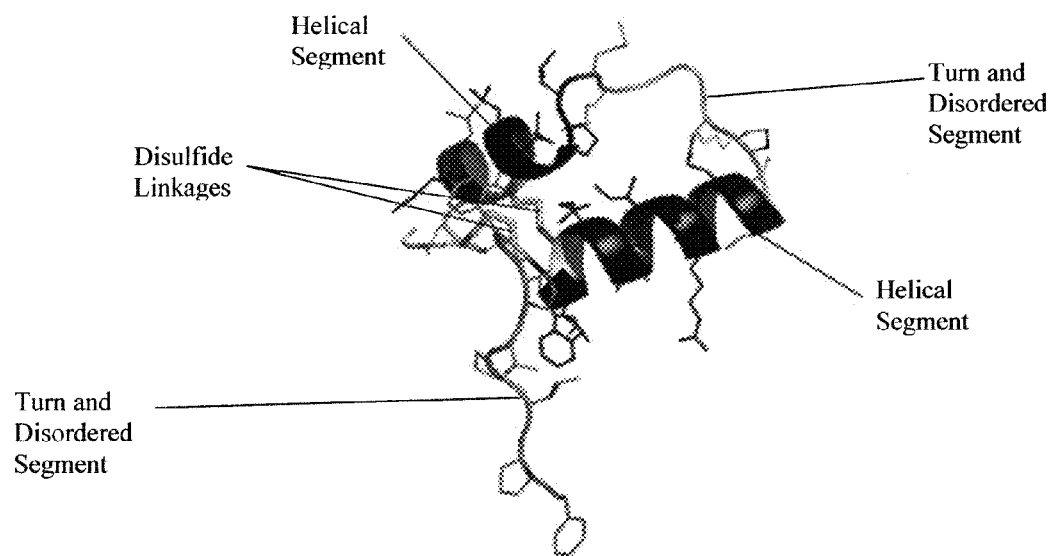
Figure 14

Figure 15
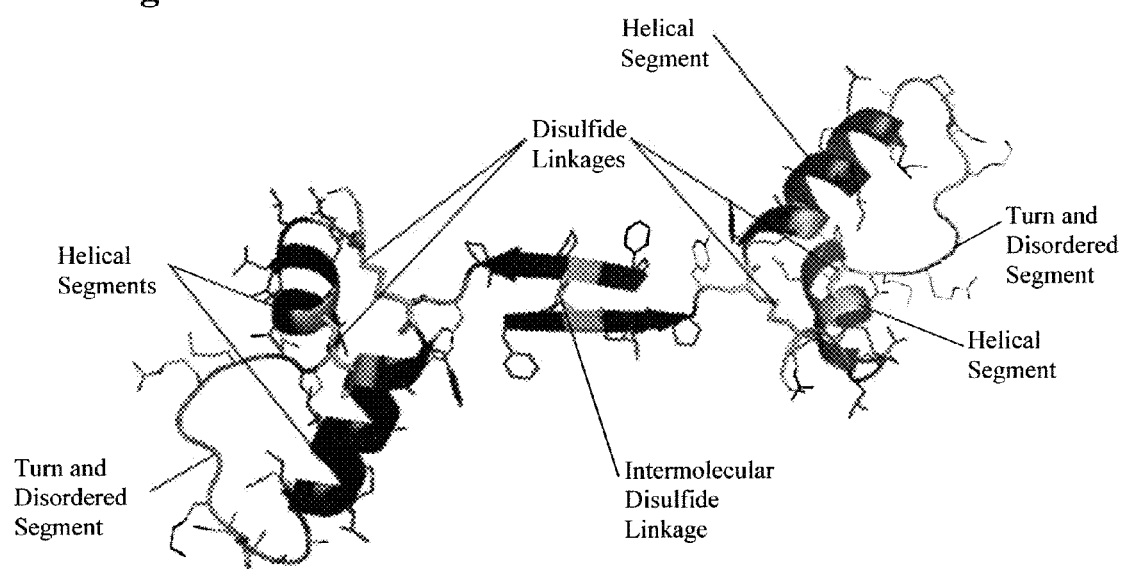
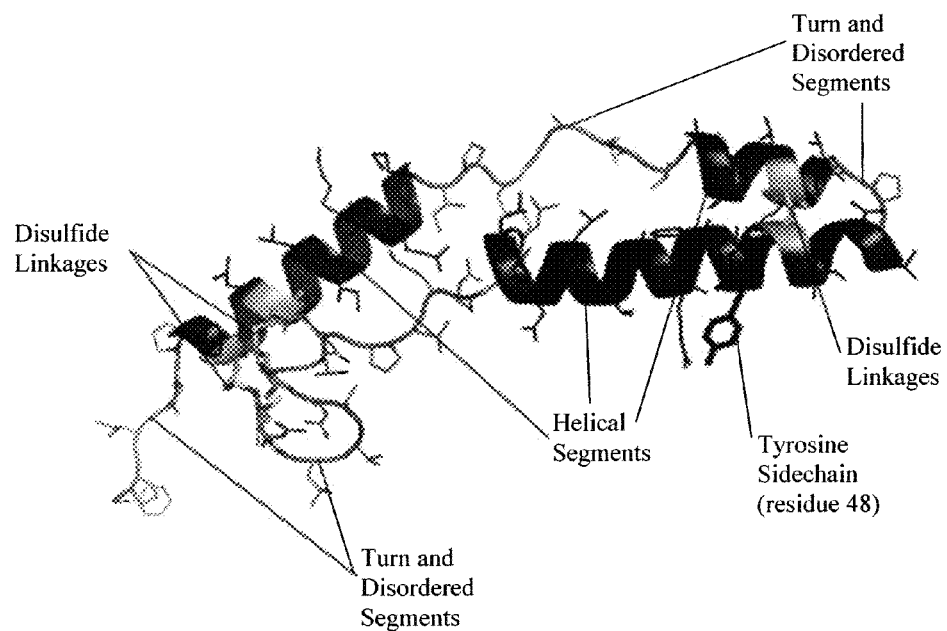
Figure 16

```
                         SEQUENCE LISTING

<160> NUMBER OF SEQ ID NOS: 30

<210> SEQ ID NO 1
<211> LENGTH: 34
<212> TYPE: PRT
<213> ORGANISM: Artificial
<220> FEATURE:
<223> OTHER INFORMATION: Minimum Consensus Sequence for "Mini-B" Peptide
      Family
```

```
<220> FEATURE:
<221> NAME/KEY: misc_feature
<222> LOCATION: (2)..(3)
<223> OTHER INFORMATION: can be any amino acid
<220> FEATURE:
<221> NAME/KEY: misc_feature
<222> LOCATION: (5)..(5)
<223> OTHER INFORMATION: can be lysine, arginine, histidine, aspartic
      acid, or glutamic acid
<220> FEATURE:
<221> NAME/KEY: misc_feature
<222> LOCATION: (6)..(8)
<223> OTHER INFORMATION: can be any amino acid
<220> FEATURE:
<221> NAME/KEY: misc_feature
<222> LOCATION: (9)..(10)
<223> OTHER INFORMATION: can be lysine, arginine, histidine, aspartic
      acid, or glutamic acid
<220> FEATURE:
<221> NAME/KEY: misc_feature
<222> LOCATION: (11)..(11)
<223> OTHER INFORMATION: can be any amino acid
<220> FEATURE:
<221> NAME/KEY: misc_feature
<222> LOCATION: (12)..(12)
<223> OTHER INFORMATION: can be lysine arginine, histidine, aspartic
      acid, or glutamic acid
<220> FEATURE:
<221> NAME/KEY: misc_feature
<222> LOCATION: (13)..(15)
<223> OTHER INFORMATION: can be any amino acid
<220> FEATURE:
<221> NAME/KEY: misc_feature
<222> LOCATION: (17)..(17)
<223> OTHER INFORMATION: can be lysine, arginine, histidine, aspartic
      acid, or glutamic acid
<220> FEATURE:
<221> NAME/KEY: misc_feature
<222> LOCATION: (18)..(19)
<223> OTHER INFORMATION: can be any amino acid
<220> FEATURE:
<221> NAME/KEY: misc_feature
<222> LOCATION: (20)..(20)
<223> OTHER INFORMATION: can be lysine, arginine, histidine, aspartic
      acid, or glutamic acid
<220> FEATURE:
<221> NAME/KEY: misc_feature
<222> LOCATION: (21)..(22)
<223> OTHER INFORMATION: can be any amino acid
<220> FEATURE:
<221> NAME/KEY: misc_feature
<222> LOCATION: (24)..(24)
<223> OTHER INFORMATION: can be lysine, arginine, histidine, aspartic
      acid, or glutamic acid
<220> FEATURE:
<221> NAME/KEY: misc_feature
<222> LOCATION: (25)..(26)
<223> OTHER INFORMATION: can be any amino acid
<220> FEATURE:
<221> NAME/KEY: misc_feature
<222> LOCATION: (28)..(28)
<223> OTHER INFORMATION: can be lysine, arginine, histidine, aspartic
      acid, or glutamic acid
<220> FEATURE:
<221> NAME/KEY: misc_feature
<222> LOCATION: (29)..(31)
<223> OTHER INFORMATION: can be any amino acid
<220> FEATURE:
<221> NAME/KEY: misc_feature
<222> LOCATION: (32)..(32)
<223> OTHER INFORMATION: can be lysine, arginine, histidine, aspartic
      acid, or glutamic acid
<220> FEATURE:
<221> NAME/KEY: misc_feature
<222> LOCATION: (34)..(34)
<223> OTHER INFORMATION: can be lysine, arginine, histidine, aspartic
      acid, or glutamic acid

<400> SEQUENCE: 1
```

Cys Xaa Xaa Cys Xaa Xaa Xaa Xaa Xaa Xaa Xaa Xaa Xaa Xaa Pro
1               5                   10                  15

Xaa Xaa Xaa Xaa Xaa Pro Xaa Xaa Xaa Cys Xaa Xaa Xaa Xaa Xaa
            20                  25                  30

Cys Xaa

<210> SEQ ID NO 2
<211> LENGTH: 71
<212> TYPE: PRT
<213> ORGANISM: Artificial
<220> FEATURE:
<223> OTHER INFORMATION: Minimum Consensus Sequence for "Maxi-B" Peptide
      Family
<220> FEATURE:
<221> NAME/KEY: misc_feature
<222> LOCATION: (2)..(3)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (5)..(5)
<223> OTHER INFORMATION: can be lysine, arginine, histidine, aspartic
      acid, or glutamic acid
<220> FEATURE:
<221> NAME/KEY: misc_feature
<222> LOCATION: (6)..(8)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (9)..(10)
<223> OTHER INFORMATION: can be lysine, arginine, histidine, aspartic
      acid, or glutamic acid
<220> FEATURE:
<221> NAME/KEY: misc_feature
<222> LOCATION: (11)..(15)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (17)..(17)
<223> OTHER INFORMATION: can be lysine, arginine, histidine, aspartic
      acid, or glutamic acid
<220> FEATURE:
<221> NAME/KEY: misc_feature
<222> LOCATION: (18)..(27)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (29)..(29)
<223> OTHER INFORMATION: can be lysine, arginine, histidine, aspartic
      acid, or glutamic acid
<220> FEATURE:
<221> NAME/KEY: misc_feature
<222> LOCATION: (30)..(31)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (33)..(38)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (40)..(40)
<223> OTHER INFORMATION: can be valine, isoleucine, leucine, methionine,
      phenylalanine, tryptophan, tyrosine, cysteine, glycine, alanine,
      proline asparagine, glutamine, or serine

```
<220> FEATURE:
<221> NAME/KEY: misc_feature
<222> LOCATION: (41)..(41)
<223> OTHER INFORMATION: can be alanine, phenylalanine or tyrosine
<220> FEATURE:
<221> NAME/KEY: misc_feature
<222> LOCATION: (42)..(43)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (44)..(44)
<223> OTHER INFORMATION: can be glutamic acid when residue 45 is
      arginine, or aspartic acid when residue 45 is lysine
<220> FEATURE:
<221> NAME/KEY: misc_feature
<222> LOCATION: (45)..(45)
<223> OTHER INFORMATION: can be arginine when residue 44 is glutamic
      acid, or lysine when residue 44 is aspartic acid
<220> FEATURE:
<221> NAME/KEY: misc_feature
<222> LOCATION: (46)..(46)
<223> OTHER INFORMATION: can be lysine, arginine, histidine, aspartic
      acid, or glutamic acid
<220> FEATURE:
<221> NAME/KEY: misc_feature
<222> LOCATION: (48)..(51)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (52)..(53)
<223> OTHER INFORMATION: can be lysine, arginine, histidine, aspartic
      acid, or glutamic acid
<220> FEATURE:
<221> NAME/KEY: misc_feature
<222> LOCATION: (54)..(56)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (57)..(57)
<223> OTHER INFORMATION: can be lysine, arginine, histidine, aspartic
      acid, or glutamic acid
<220> FEATURE:
<221> NAME/KEY: misc_feature
<222> LOCATION: (58)..(59)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (61)..(63)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (65)..(65)
<223> OTHER INFORMATION: can be lysine, arginine, histidine, aspartic
      acid, or glutamic acid
<220> FEATURE:
<221> NAME/KEY: misc_feature
<222> LOCATION: (66)..(68)
<223> OTHER INFORMATION: can be valine, isoleucine, leucine, methionine,
      phenylalanine, tryptophan, tyrosine, cysteine, glycine, alanine,
      proline asparagine, glutamine, or serine
<220> FEATURE:
<221> NAME/KEY: misc_feature
<222> LOCATION: (69)..(69)
<223> OTHER INFORMATION: can be lysine, arginine, histidine, aspartic
      acid, or glutamic acid
<220> FEATURE:
<221> NAME/KEY: misc_feature
<222> LOCATION: (71)..(71)
<223> OTHER INFORMATION: can be lysine, arginine, histidine, aspartic
``` acid, or glutamic acid

<400> SEQUENCE: 2

Cys Xaa Xaa Cys Xaa Xaa Xaa Xaa Xaa Xaa Xaa Xaa Xaa Xaa Xaa Pro
1               5                   10                  15

Xaa Xaa Xaa Xaa Xaa Xaa Xaa Xaa Xaa Xaa Cys Xaa Xaa Xaa Pro
            20                  25                  30

Xaa Xaa Xaa Xaa Xaa Xaa Cys Xaa Xaa Xaa Xaa Xaa Xaa Ser Xaa
        35                  40                  45

Xaa Xaa Xaa Xaa Xaa Xaa Xaa Xaa Xaa Xaa Pro Xaa Xaa Xaa Cys
    50                  55                  60

Xaa Xaa Xaa Xaa Xaa Cys Xaa
65                  70

<210> SEQ ID NO 3
<211> LENGTH: 35
<212> TYPE: PRT
<213> ORGANISM: Artificial
<220> FEATURE:
<223> OTHER INFORMATION: Minimum Consensus Sequence for Peptide Family
<220> FEATURE:
<221> NAME/KEY: misc_feature
<222> LOCATION: (5)..(6)
<223> OTHER INFORMATION: can be phenylalanine, cysteine residues that
      are thioester-linked to palmitate, or lysine residues that are
      amide-linked to palmitate
<220> FEATURE:
<221> NAME/KEY: misc_feature
<222> LOCATION: (13)..(14)
<223> OTHER INFORMATION: can be leucine or proline
<220> FEATURE:
<221> NAME/KEY: misc_feature
<222> LOCATION: (15)..(21)
<223> OTHER INFORMATION: can be valine or proline
<220> FEATURE:
<221> NAME/KEY: misc_feature
<222> LOCATION: (22)..(22)
<223> OTHER INFORMATION: can be leucine or proline
<220> FEATURE:
<221> NAME/KEY: misc_feature
<222> LOCATION: (23)..(26)
<223> OTHER INFORMATION: can be valine or proline
<220> FEATURE:
<221> NAME/KEY: misc_feature
<222> LOCATION: (27)..(27)
<223> OTHER INFORMATION: can be isoleucine or proline
<220> FEATURE:
<221> NAME/KEY: misc_feature
<222> LOCATION: (28)..(28)
<223> OTHER INFORMATION: can be valine or proline
<220> FEATURE:
<221> NAME/KEY: misc_feature
<222> LOCATION: (29)..(29)
<223> OTHER INFORMATION: can be glycine or proline
<220> FEATURE:
<221> NAME/KEY: misc_feature
<222> LOCATION: (30)..(30)
<223> OTHER INFORMATION: can be alanine or proline
<220> FEATURE:
<221> NAME/KEY: misc_feature
<222> LOCATION: (31)..(32)
<223> OTHER INFORMATION: can be leucine or proline
<220> FEATURE:
<221> NAME/KEY: misc_feature
<222> LOCATION: (33)..(33)
<223> OTHER INFORMATION: can be methionine or proline

<400> SEQUENCE: 3

Phe Gly Ile Pro Xaa Xaa Pro Val His Leu Lys Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa

-continued

```
                    20                  25                  30

Xaa Gly Leu
        35

<210> SEQ ID NO 4
<211> LENGTH: 34
<212> TYPE: PRT
<213> ORGANISM: Artificial
<220> FEATURE:
<223> OTHER INFORMATION: Mini-B peptide

<400> SEQUENCE: 4

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 5
<211> LENGTH: 34
<212> TYPE: PRT
<213> ORGANISM: Artificial
<220> FEATURE:
<223> OTHER INFORMATION: Mini-B peptide variant with FK helix hairpin

<400> SEQUENCE: 5

Cys Trp Phe Cys Arg Phe Phe Phe Lys Arg Phe Phe Phe Phe Phe Pro
1               5                   10                  15

Lys Gly Gly Arg Phe Phe Pro Phe Phe Phe Cys Arg Phe Phe Phe Arg
            20                  25                  30

Cys Ser

<210> SEQ ID NO 6
<211> LENGTH: 34
<212> TYPE: PRT
<213> ORGANISM: Artificial
<220> FEATURE:
<223> OTHER INFORMATION: Mini-B peptide variant with Phe-N-terminal
      helix

<400> SEQUENCE: 6

Cys Trp Phe Cys Arg Ala Phe Ile Lys Arg Phe Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 7
<211> LENGTH: 34
<212> TYPE: PRT
<213> ORGANISM: Artificial
<220> FEATURE:
<223> OTHER INFORMATION: Mini-B peptide variant

<400> SEQUENCE: 7

Cys Trp Leu Cys Arg Ala Leu Ile Lys Arg Ile Gln Ala Met Ile Pro
1               5                   10                  15

Lys Gly Gly Arg Met Phe Pro Gln Phe Phe Cys Arg Phe Phe Phe Arg
            20                  25                  30

Cys Ser
```

<210> SEQ ID NO 8
<211> LENGTH: 34
<212> TYPE: PRT
<213> ORGANISM: Artificial
<220> FEATURE:
<223> OTHER INFORMATION: Min-B peptide variant

<400> SEQUENCE: 8

Cys Trp Phe Cys Arg Ala Phe Ile Lys Arg Phe Gln Ala Met Ile Pro
1               5                   10                  15

Lys Gly Gly Arg Met Phe Pro Gln Phe Phe Cys Arg Phe Phe Phe Arg
            20                  25                  30

Cys Ser

<210> SEQ ID NO 9
<211> LENGTH: 34
<212> TYPE: PRT
<213> ORGANISM: Artificial
<220> FEATURE:
<223> OTHER INFORMATION: Mini-B peptide variant

<400> SEQUENCE: 9

Cys Trp Phe Cys Arg Ala Phe Ile Lys Arg Phe Gln Ala Met Ile Pro
1               5                   10                  15

Lys Gly Glu Arg Met Leu Pro Gln Leu Val Cys Arg Leu Val Leu Arg
            20                  25                  30

Cys Ser

<210> SEQ ID NO 10
<211> LENGTH: 34
<212> TYPE: PRT
<213> ORGANISM: Artificial
<220> FEATURE:
<223> OTHER INFORMATION: Mini-B peptide variant

<400> SEQUENCE: 10

Cys Trp Leu Cys Arg Ala Leu Ile Lys Arg Ile Gln Ala Met Ile Pro
1               5                   10                  15

Lys Gly Glu Arg Met Phe Pro Gln Phe Phe Cys Arg Phe Phe Phe Arg
            20                  25                  30

Cys Ser

<210> SEQ ID NO 11
<211> LENGTH: 34
<212> TYPE: PRT
<213> ORGANISM: Artificial
<220> FEATURE:
<223> OTHER INFORMATION: Mini-B peptide variant

<400> SEQUENCE: 11

Cys Trp Phe Cys Arg Ala Phe Ile Lys Arg Phe Gln Ala Met Ile Pro
1               5                   10                  15

Lys Gly Glu Arg Met Phe Pro Gln Phe Phe Cys Arg Phe Phe Phe Arg
            20                  25                  30

Cys Ser

<210> SEQ ID NO 12
<211> LENGTH: 34
<212> TYPE: PRT
<213> ORGANISM: Artificial
<220> FEATURE:
<223> OTHER INFORMATION: Mini-B dimer with Lys17-Cys17
<220> FEATURE:

```
<221> NAME/KEY: misc_feature
<222> LOCATION: (17)..(17)
<223> OTHER INFORMATION: can be a lysine-derivatized cysteine residue

<400> SEQUENCE: 12

Cys Trp Leu Cys Arg Ala Leu Ile Lys Arg Ile Gln Ala Met Ile Pro
1               5                   10                  15

Xaa Gly Gly Arg Met Leu Pro Gln Leu Val Cys Arg Leu Val Leu Arg
            20                  25                  30

Cys Ser

<210> SEQ ID NO 13
<211> LENGTH: 41
<212> TYPE: PRT
<213> ORGANISM: Artificial
<220> FEATURE:
<223> OTHER INFORMATION: Super Mini-B peptide

<400> SEQUENCE: 13

Phe Pro Ile Pro Leu Pro Tyr Cys Trp Leu Cys Arg Ala Leu Ile Lys
1               5                   10                  15

Arg Ile Gln Ala Met Ile Pro Lys Gly Gly Arg Met Leu Pro Gln Leu
            20                  25                  30

Val Cys Arg Leu Val Leu Arg Cys Ser
        35                  40

<210> SEQ ID NO 14
<211> LENGTH: 41
<212> TYPE: PRT
<213> ORGANISM: Artificial
<220> FEATURE:
<223> OTHER INFORMATION: Super Mini-B variant

<400> SEQUENCE: 14

Phe Pro Cys Pro Leu Pro Tyr Cys Trp Leu Cys Arg Ala Leu Ile Lys
1               5                   10                  15

Arg Ile Gln Ala Met Ile Pro Lys Gly Gly Arg Met Leu Pro Gln Leu
            20                  25                  30

Val Cys Arg Leu Val Leu Arg Cys Ser
        35                  40

<210> SEQ ID NO 15
<211> LENGTH: 41
<212> TYPE: PRT
<213> ORGANISM: Artificial
<220> FEATURE:
<223> OTHER INFORMATION: Super Mini-B variant

<400> SEQUENCE: 15

Cys Pro Ile Pro Leu Pro Tyr Cys Trp Leu Cys Arg Ala Leu Ile Lys
1               5                   10                  15

Arg Ile Gln Ala Met Ile Pro Lys Gly Gly Arg Met Leu Pro Gln Leu
            20                  25                  30

Val Cys Arg Leu Val Leu Arg Cys Ser
        35                  40

<210> SEQ ID NO 16
<211> LENGTH: 71
<212> TYPE: PRT
<213> ORGANISM: Artificial
<220> FEATURE:
<223> OTHER INFORMATION: Maxi-B peptide
```

```
<400> SEQUENCE: 16

Cys Trp Leu Cys Arg Ala Leu Ile Lys Arg Ile Gln Ala Met Ile Pro
1               5                   10                  15

Lys Gly Ala Leu Ala Val Ala Val Ala Gln Val Cys Arg Val Val Pro
                20                  25                  30

Leu Val Ala Gly Gly Ile Cys Gln Ala Leu Ala Glu Arg Tyr Ser Val
            35                  40                  45

Ile Leu Leu Asp Thr Leu Leu Gly Arg Met Leu Pro Gln Leu Val Cys
50                  55                  60

Arg Leu Val Leu Arg Cys Ser
65                  70

<210> SEQ ID NO 17
<211> LENGTH: 71
<212> TYPE: PRT
<213> ORGANISM: Artificial
<220> FEATURE:
<223> OTHER INFORMATION: Maxi-B Phe peptide

<400> SEQUENCE: 17

Cys Trp Leu Cys Arg Ala Leu Ile Lys Arg Ile Gln Ala Met Ile Pro
1               5                   10                  15

Lys Gly Ala Leu Ala Val Ala Val Ala Gln Val Cys Arg Val Val Pro
                20                  25                  30

Leu Val Ala Gly Gly Ile Cys Gln Phe Leu Ala Glu Arg Tyr Ser Val
            35                  40                  45

Ile Leu Leu Asp Thr Leu Leu Gly Arg Met Leu Pro Gln Leu Val Cys
50                  55                  60

Arg Leu Val Leu Arg Cys Ser
65                  70

<210> SEQ ID NO 18
<211> LENGTH: 78
<212> TYPE: PRT
<213> ORGANISM: Artificial
<220> FEATURE:
<223> OTHER INFORMATION: Super Maxi-B peptide

<400> SEQUENCE: 18

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
                20                  25                  30

Gln Val Cys Arg Val Val Pro Leu Val Val Gly Gly Ile Cys Gln Tyr
            35                  40                  45

Leu Ala Glu Arg Tyr Ser Val Ile Leu Leu Asp Thr Leu Leu Gly Arg
        50                  55                  60

Met Leu Pro Gln Leu Val Cys Arg Leu Val Leu Arg Cys Ser
65                  70                  75

<210> SEQ ID NO 19
<211> LENGTH: 78
<212> TYPE: PRT
<213> ORGANISM: Artificial
<220> FEATURE:
<223> OTHER INFORMATION: Super Maxi-B dimer with Cys1

<400> SEQUENCE: 19

Cys Pro Ile Pro Leu Pro Tyr Cys Trp Leu Cys Arg Ala Leu Ile Lys
1               5                   10                  15
```

```
Arg Ile Gln Ala Met Ile Pro Lys Gly Ala Leu Ala Val Ala Val Ala
            20                  25                  30

Gln Val Cys Arg Val Val Pro Leu Val Val Gly Gly Ile Cys Gln Tyr
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser
65                  70                  75

<210> SEQ ID NO 20
<211> LENGTH: 78
<212> TYPE: PRT
<213> ORGANISM: Artificial
<220> FEATURE:
<223> OTHER INFORMATION: Super Maxi-B dimer with Cys3

<400> SEQUENCE: 20

Phe Pro Cys Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Val Gly Gly Ile Cys Gln Tyr
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser
65                  70                  75

<210> SEQ ID NO 21
<211> LENGTH: 35
<212> TYPE: PRT
<213> ORGANISM: Artificial
<220> FEATURE:
<223> OTHER INFORMATION: SP-C FF peptide

<400> SEQUENCE: 21

Phe Gly Ile Pro Phe Phe Pro Val His Leu Lys Arg Leu Leu Val Val
1               5                   10                  15

Val Val Val Val Val Leu Val Val Val Ile Val Gly Ala Leu Leu
            20                  25                  30

Met Gly Leu
        35

<210> SEQ ID NO 22
<211> LENGTH: 35
<212> TYPE: PRT
<213> ORGANISM: Artificial
<220> FEATURE:
<223> OTHER INFORMATION: SP-C FF Pro16 peptide

<400> SEQUENCE: 22

Phe Gly Ile Pro Phe Phe Pro Val His Leu Lys Arg Leu Leu Val Pro
1               5                   10                  15

Val Val Val Val Val Leu Val Val Val Ile Val Gly Ala Leu Leu
            20                  25                  30

Met Gly Leu
        35

<210> SEQ ID NO 23
<211> LENGTH: 35
```

```
<212> TYPE: PRT
<213> ORGANISM: Artificial
<220> FEATURE:
<223> OTHER INFORMATION: SP-C FF Pro20 peptide

<400> SEQUENCE: 23

Phe Gly Ile Pro Phe Phe Pro Val His Leu Lys Arg Leu Leu Val Val
1               5                   10                  15

Val Val Val Pro Val Leu Val Val Val Ile Val Gly Ala Leu Leu
            20                  25                  30

Met Gly Leu
        35

<210> SEQ ID NO 24
<211> LENGTH: 35
<212> TYPE: PRT
<213> ORGANISM: Artificial
<220> FEATURE:
<223> OTHER INFORMATION: SP-C FF Pro24 peptide

<400> SEQUENCE: 24

Phe Gly Ile Pro Phe Phe Pro Val His Leu Lys Arg Leu Leu Val Val
1               5                   10                  15

Val Val Val Val Leu Val Pro Val Ile Val Gly Ala Leu Leu
            20                  25                  30

Met Gly Leu
        35

<210> SEQ ID NO 25
<211> LENGTH: 35
<212> TYPE: PRT
<213> ORGANISM: Artificial
<220> FEATURE:
<223> OTHER INFORMATION: SP-C FF Pro28 peptide

<400> SEQUENCE: 25

Phe Gly Ile Pro Phe Phe Pro Val His Leu Lys Arg Leu Leu Val Val
1               5                   10                  15

Val Val Val Val Val Leu Val Val Val Ile Pro Gly Ala Leu Leu
            20                  25                  30

Met Gly Leu
        35

<210> SEQ ID NO 26
<211> LENGTH: 20
<212> TYPE: PRT
<213> ORGANISM: Artificial
<220> FEATURE:
<223> OTHER INFORMATION: poly-KF peptide

<400> SEQUENCE: 26

Phe Lys Phe Lys Phe Lys Phe Lys Phe Lys Phe Lys Phe Lys Phe Lys
1               5                   10                  15

Phe Lys Phe Lys
            20

<210> SEQ ID NO 27
<211> LENGTH: 21
<212> TYPE: PRT
<213> ORGANISM: Artificial
<220> FEATURE:
<223> OTHER INFORMATION: F4K peptide

<400> SEQUENCE: 27
```

```
Lys Phe Phe Phe Phe Lys Phe Phe Phe Lys Phe Phe Phe Lys
1               5                   10                  15

Phe Phe Phe Phe Lys
            20

<210> SEQ ID NO 28
<211> LENGTH: 20
<212> TYPE: PRT
<213> ORGANISM: Artificial
<220> FEATURE:
<223> OTHER INFORMATION: poly-FR peptide

<400> SEQUENCE: 28

Phe Arg Phe Arg Phe Arg Phe Arg Phe Arg Phe Arg Phe Arg Phe Arg
1               5                   10                  15

Phe Arg Phe Arg
            20

<210> SEQ ID NO 29
<211> LENGTH: 21
<212> TYPE: PRT
<213> ORGANISM: Artificial
<220> FEATURE:
<223> OTHER INFORMATION: F4R peptide

<400> SEQUENCE: 29

Arg Phe Phe Phe Phe Arg Phe Phe Phe Phe Arg Phe Phe Phe Phe Arg
1               5                   10                  15

Phe Phe Phe Phe Arg
            20

<210> SEQ ID NO 30
<211> LENGTH: 21
<212> TYPE: PRT
<213> ORGANISM: Artificial
<220> FEATURE:
<223> OTHER INFORMATION: R-F4K peptide

<400> SEQUENCE: 30

Arg Phe Phe Phe Phe Lys Phe Phe Phe Phe Arg Phe Phe Phe Phe Arg
1               5                   10                  15

Phe Phe Phe Phe Lys
            20
```

SYNTHETIC LUNG SURFACTANT AND USE THEREOF

This application is a division of U.S. patent application Ser. No. 12/374,458, which is a national stage application under 35 U.S.C. 371 of PCT/US2007/073390, filed Jul. 20, 2007, which claims the priority benefit of U.S. Provisional Patent Application Ser. No. 60/807,933, filed Jul. 20, 2006, each of which is hereby incorporated by reference in its entirety.

This invention was made with government support under grant numbers R01 HL-56176, R01 HL-25170, R01 HL-32242, KO4-HL-00945, P50 HL-36543, and R01 HL-55534 awarded by the National Institutes of Health. The government has certain rights in the invention.

FIELD OF THE INVENTION

The present invention relates to synthetic lung surfactant compositions, novel peptides and/or phospholipase-resistant phosphatidylglycerol derivatives for use in the surfactant compositions, and various uses of the surfactant compositions.

BACKGROUND OF THE INVENTION

The airsacs in the lungs of mammals are stabilized by pulmonary surfactant, a complex mixture containing glycerophospholipids and specific surfactant proteins (SP) that is synthesized by type II epithelial cells in the alveolar lining (for review see text by Notter (Notter, *Lung Surfactants: Basic Science and Clinical Applications*, Marcel Dekker, Inc, New York (2000)). The mammalian lungs have a huge internal surface of the order 1 m²/kg body weight at total lung capacity, and much of this surface is lined by a thin liquid film or "alveolar hypophase". Surface tension forces at the extensive air-hypophase interface are a major contributor to the work of breathing. Pulmonary surfactant plays crucial roles in respiratory physiology by moderating these surface tension forces. Endogenous surfactant secreted by alveolar type II epithelial cells adsorbs at the air-hypophase interface and lowers and varies surface tension as a function of alveolar size during breathing. This regulation of surface tension reduces the work of breathing while stabilizing alveoli against collapse and overdistension. It also leads to a smaller hydrostatic pressure driving force for edema fluid to move into the lung interstitium from the pulmonary capillaries. Functional pulmonary surfactant is necessary for life, and its deficiency or dysfunction is associated with severe impairments in respiratory function that can be lethal if not treated effectively.

A major disease where lung surfactant deficiency causes respiratory failure is the neonatal respiratory distress syndrome ("RDS"), also called Hyaline Membrane Disease ("HMD"). RDS is most prevalent in premature infants <32 weeks gestation (term=40 weeks in humans), but it can also occur in older premature infants of 32-36 weeks gestation. RDS is caused by a deficiency of endogenous surfactant in the lungs of premature infants at birth (although elements of lung injury with acquired surfactant dysfunction can subsequently arise during its clinical course). The major clinical conditions associated with lung surfactant dysfunction are the syndromes of acute lung injury ("ALI") and the acute respiratory distress syndrome ("ARDS"). ALI and ARDS are lethal manifestations of inflammatory lung injury that can result from multiple direct and indirect causes ranging from respiratory infection, gastric aspiration, meconium aspiration, hyperoxia, near drowning, chest trauma, hypovolemic shock, bacterial sepsis, and many others (for review see Notter et al., editors, *Lung Injury: Mechanisms, Pathophysiology and Therapy*, Taylor Francis Group, Inc, Boca Raton (2005)). ALI/ARDS can affect patients of any age from infants to adults, although different age groups vary somewhat in the etiology and specifics of disease. The American-European Consensus Committee in 1994 defined clinical ARDS more specifically as requiring an acute onset, bilateral infiltrates on frontal chest radiograph, a $PaO_2/FiO_2$ ratio ≤200 mmHg, and a pulmonary capillary wedge pressure ≤18 mmHg (if measured) or no evidence of left atrial hypertension (Bernard et al., "The American-European Consensus Conference on ARDS: Definitions, Mechanisms, Relevant Outcomes, and Clinical Trial Coordination," *Am J Respir Crit Care Med* 149:818-824 (1994)). The Consensus Committee defined ALI identically to ARDS except for a $PaO_2/FiO_2$ ratio ≤300 mmHg (Bernard et al., "The American-European Consensus Conference on ARDS: Definitions, Mechanisms, Relevant Outcomes, and Clinical Trial Coordination," *Am J Respir Crit Care Med* 149:818-824 (1994)) (all patients with ARDS by definition also have ALI). ALI/ARDS affects 50,000 to 150,000 patients in the United States each year (estimates range as high as 64 cases per 100,000 people per year), and has substantial mortality rates of 30-50% despite sophisticated intensive care (Bernard et al., "The American-European Consensus Conference on ARDS: Definitions, Mechanisms, Relevant Outcomes, and Clinical Trial Coordination," *Am J Respir Crit Care Med* 149:818-824 (1994); Hudson et al., "Clinical Risks for Development of the Acute Respiratory Distress Syndrome," *Am J Respir Crit Care Med* 151:293-301 (1995); Hyers, "Prediction of Survival and Mortality in Patients With the Adult Respiratory Distress Syndrome," *New Horizons* 1:466-470 (1993); Doyle et al., "Identification of Patients With Acute Lung Injury: Predictors of Mortality," *Am J Respir Crit Care Med* 152:1818-1824 (1995); Milberg et al., "Improved Survival of Patients With Acute Respiratory Distress Syndrome," *JAMA* 273:306-309 (1995); Krafft et al., "The Acute Respiratory Distress Syndrome; Definitions, Severity, and Clinical Outcome. An Analysis of 101 Clinical Investigations," *Intensive Care Med* 22:519-529 (1996); Goss et al., "Incidence of Acute Lung Injury in the United States," *Crit Care Med* 31:1607-1611 (2003)). Multiple studies have identified surfactant abnormalities in bronchoalveolar lavage (lung washings) from patients with ALI/ARDS (e.g., Petty et al., "Characteristics of Pulmonary Surfactant in Adult Respiratory Distress Syndrome Associated With Trauma and Shock," *Am Rev Respir Dis* 115:531-536 (1977); Hallman et al., "Evidence of Lung Surfactant Abnormality in Respiratory Failure," *J Clin Invest* 70:673-683 (1982); Seeger et al., "Surfactant Abnormalities and Adult Respiratory Failure," *Lung* 168 (Suppl):891-902 (1990); Pison et al., "Surfactant Abnormalities in Patients With Respiratory Failure After Multiple Trauma," *Am Rev Respir Dis* 140:1033-1039 (1989); Gregory et al., "Surfactant Chemical Composition and Biophysical Activity in Acute Respiratory Distress Syndrome," *J Clin Invest* 88:1976-1981 (1991); Veldhuizen et al., "Pulmonary Surfactant Subfractions in Patients With the Acute Respiratory Distress Syndrome," *Am J Respir Crit Care Med* 152:1867-1871 (1995); Griese, "Pulmonary Surfactant in Health and Human Lung Diseases: State of the Art," *Eur Respir J* 13:1455-1476 (1999); Gunther et al., "Surfactant Alterations in Severe Pneumonia, Acute Respiratory Distress Syndrome, and Cardiogenic Lung Edema," *Am J Respir Crit Care Med* 153:176-184 (1996)).

Surfactant dysfunction in ALI/ARDS occurs by several mechanisms including physical and chemical interactions with inhibitors in edema fluid or lung tissue (Notter, *Lung Surfactants: Basic Science and Clinical Applications*, Marcel Dekker, Inc, New York (2000); Notter et al., "Pulmonary Surfactant: Physical Chemistry, Physiology and Replacement," *Rev Chem Eng* 13:1-118 (1997); Wang et al., "Surfactant Activity and Dysfunction in Lung Injury," In Notter et al., editors, *Lung Injury: Mechanisms, Pathophysiology, and Therapy*, Taylor Francis Group, Inc, Boca Raton, pp. 297-352 (2005)). To be optimally effective, exogenous surfactants used in treating ALI/ARDS and/or severe RDS must have very high surface activity and resistance to biophysical inhibition and/or chemical degradation.

Exogenous surfactant therapy is straightforward in concept, i.e., if endogenous surfactant is deficient or becomes dysfunctional, then it can be replaced or supplemented by the delivery of active exogenous surface-active material to the alveoli by airway instillation or by other techniques such as aerosolization or nebulization. Exogenous surfactant therapy is intended to preserve lung function over the short term while the patient's lungs develop or recover the ability to produce and maintain adequate levels of endogenous surfactant. The utility of exogenous surfactant therapy to prevent or treat RDS in premature infants is now well documented by an extensive body of literature (Notter, *Lung Surfactants: Basic Science and Clinical Applications*, Marcel Dekker, Inc, New York (2000); Soll, "Surfactant Therapy in The USA: Trials and Current Routines," *Biol Neonate* 71:1-7 (1997); Soll et al., "Surfactant in the Prevention and Treatment of Respiratory Distress Syndrome," In *New Therapies for Neonatal Respiratory Failure*, Boynton et al., editors, Cambridge University Press, New York, pp. 49-80 (1994); Jobe, "Pulmonary Surfactant Therapy," *N Engl J Med* 328:861-868 (1993)). Exogenous surfactant therapy is still under development for ALI/ARDS, although basic research and the known existence of surfactant dysfunction in patients with this condition provide a clear conceptual rationale for the potential benefits of such therapy (Chess et al., "Surfactant Replacement Therapy in Lung Injury," In *Lung Injury: Mechanisms, Pathophysiology, and Therapy*, Notter et al., editors, Taylor Francis Group, Inc, Boca Raton, pp. 617-663 (2005)).

Published research shows that current animal-derived clinical exogenous surfactants, e.g., Infasurf® (CLSE), Survanta®, and Curosurf®, are more active biophysically and physiologically than available synthetic surfactants such as Exosurf® and ALEC (Notter, *Lung Surfactants: Basic Science and Clinical Applications*, Marcel Dekker, Inc, New York (2000); Soll, "Surfactant Therapy in The USA: Trials and Current Routines," *Biol Neonate* 71:1-7 (1997); Soll et al., "Surfactant in the Prevention and Treatment of Respiratory Distress Syndrome," In *New Therapies for Neonatal Respiratory Failure*, Boynton et al., editors, Cambridge University Press, New York, pp. 49-80 (1994); Jobe, "Pulmonary Surfactant Therapy," *N Engl J Med* 328:861-868 (1993)). However, synthetic lung surfactants manufactured under controlled conditions in the laboratory have significant potential advantages in purity, compositional reproducibility, activity reproducibility, and manufacturing quality control compared to animal-derived preparations. In addition, constituents in synthetic surfactants can be designed with special and useful molecular properties. As biological products, FDA-approved animal-derived exogenous surfactants have complex compositional limits and significant batch-to-batch variability, which increases the cost and number of required monitoring tests during manufacture including added bioassays and activity assays. Synthetic drugs in principle become increasingly cost-effective over time once development costs are recovered. Synthetic surfactants are also free from concerns about prion-caused animal diseases (e.g., bovine spongioform encephalitis) that can limit animal lung supplies and increase costs, and synthetic surfactants are not subject to ethnographic (cultural and religious) considerations that can affect bovine- or porcine-derived preparations. There are currently no synthetic lung surfactant compositions that are as biophysically active as exogenous animal-derived surfactants.

The present invention is directed to overcoming these and other deficiencies in the art.

SUMMARY OF THE INVENTION

A first aspect of the present invention relates to a surfactant composition including a phospholipase-resistant phospho-glycerol derivative.

A second aspect of the present invention relates to a surfactant composition including a phospholipase-resistant phospho-choline derivative and a surface active peptide.

A third aspect of the present invention relates to a surfactant composition including a phospholipase-resistant phospho-glycerol derivative and one or both of a phospholipase-resistant phospho-choline derivative and a surface active protein or peptide.

A fourth aspect of the present invention relates to a surfactant composition including a phospholipid and a surface active peptide. According to this aspect of the present invention, the phospholipid can be a glycerophospholipid found in endogenous surfactants (including exogenous surfactant formulations) as well as a phospholipase-resistant phospho-glycerol derivative, a phospholipase-resistant phospho-choline derivative, or a combination thereof.

A fifth aspect of the present invention relates to a method of treating endogenous surfactant dysfunctional lung tissue. This includes providing a surfactant composition according to any of the first, second, third, or fourth aspects of the present invention, and administering the surfactant composition to a patient having lung tissue characterized by endogenous surfactant deficiency and/or dysfunction. The administering is carried out under conditions effective to coat alveolar surfaces of the affected lung tissue with the surfactant composition, thereby treating the surfactant deficient and/or dysfunctional lung tissue.

A sixth aspect of the present invention relates to a method of delivering a therapeutic agent. The method includes introducing a therapeutic agent into a surfactant composition according to any of the first, second, third, or fourth aspects of the present invention under conditions effective to encapsulate the therapeutic agent in liposomal vesicles. The method also involves administering the composition to a subject under conditions effective to deliver the therapeutic agent to a target tissue.

A seventh aspect of the present invention relates to novel phosphatidyl-glycerol derivatives that are characterized by phospholipase resistance. These derivatives are compounds having a structure according to formulae (Ia) or (Ib)

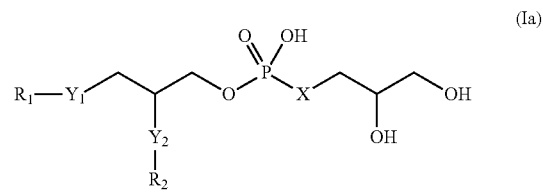

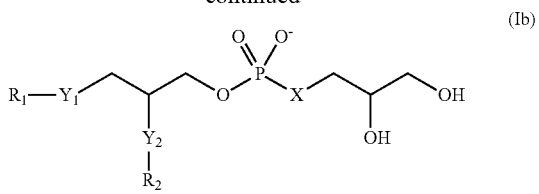

(Ib)

wherein X is O or (CH$_2$)$_n$ where n is an integer from 0 to 5; Y$_1$ and Y$_2$ are independently O, S, or SO$_2$; and R$_1$ and R$_2$ are independently C8-C24 hydrocarbons; and wherein when X, Y$_1$, and Y$_2$ are each O, R$_1$ and R$_2$ are not both saturated C14 (Ia), C15 (Ia), C16 (Ia,b), or C18 (Ia,b) hydrocarbons or unsaturated C18:1 (Ia,b) hydrocarbons, or R$_1$ is not a saturated C18 hydrocarbon when R$_2$ is a saturated C12 hydrocarbon (Ib).

An eighth aspect of the present invention relates to a synthetic peptide selected from the group consisting of any one or more of SEQ ID NOS: 1-30 or, alternatively, any one or more of SEQ ID NOS: 1-3 and 5-30 (i.e., excluding the peptide of SEQ ID NO: 4).

A ninth aspect of the present invention relates to a method of synthesizing a surface-active peptide useful in artificial lung surfactant. The method includes providing a compound according to the seventh aspect of the present invention or a surfactant composition according to the first or third aspects of the present invention, and then synthesizing a surface-active peptide in the presence of either the compound or the surfactant composition, where the compound or the composition promotes activity of the surface-active peptide, where the surface-active peptide has increased surface activity relative to a peptide synthesized in the absence of the compound or the composition.

A tenth aspect of the present invention relates to methods of making the phospholipase-resistant phospho-glycerol derivatives of the present invention. These methods include the steps of: treating an intermediate compound according to the formula

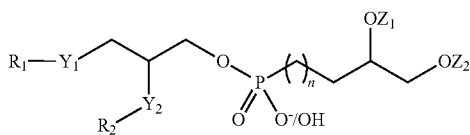

under conditions effective to form a compound according to the seventh aspect of the present invention (i.e., formula Ia or Ib) where R$_1$, R$_2$, Y$_1$, and Y$_2$ are defined above, X is (CH$_2$)$_n$, and Z$_1$ and Z$_2$ are both protecting groups, which can be the same or different.

The present invention achieves a synthetic lung surfactant composition that overcomes the above-identified deficiencies through the use of one or more of phospholipase-resistant phosphoglycerol derivatives, phospholipase-resistant phosphocholine derivatives, and synthetic surface-active peptides. In particular, several synthetic compositions of the present invention can achieve higher surface activity than animal-derived surfactants.

The synthetic lipid derivatives used in the surfactant compositions of the present invention are designed with molecular structures that are resistant to one or more endogenous phospholipases (A$_1$, A$_2$, and/or D) (Turcotte et al., "Chemical Synthesis and Surface Activity of Lung Surfactant Phospholipid Analogs. II. Racemic N-Substituted Diether Phosphonolipids," Biochim Biophys Acta 1084:1-12 (1991); Turcotte et al., "Chemical Synthesis and Surface Properties of an Analog of the Pulmonary Surfactant Dipalmitoyl Phosphatidylcholine Analog," Biochim Biophys Acta 488:235-248 (1977), each of which is hereby incorporated by reference in its entirety). Compounds of this type can also have partial resistance to degradation by phospholipase C (Lin et al., "A Diether Phosphonolipid Surfactant Analog, DEPN-8, is Resistant to Phospholipase-C Cleavage," Respiration 64:96-101 (1997), which is hereby incorporated by reference in its entirety). Phospholipase A$_2$ (PLA$_2$) is thought to play important roles in the pathogenesis of meconium aspiration syndrome (Kaapa, "Meconium Aspiration Syndrome: A Role for Phospholipase A$_2$ in the Pathogenesis?" Acta Paediatr. 90:365-367 (2001); Schrama et al., "Phospholipase A$_2$ is Present in Meconium and Inhibits the Activity of Pulmonary Surfactant: An in vitro Study," Acta Paediatr. 90:412-416 (2001)) and ARDS (Touqui et al., "A Role for Phospholipase A$_2$ in ARDS Pathogenesis," Molec Med Today 5:244-249 (1999), each of which is hereby incorporated by reference in its entirety). PLA$_2$ is present in meconium and is known to be inhibitory to surfactant function (Schrama et al., "Phospholipase A$_2$ is Present in Meconium and Inhibits the Activity of Pulmonary Surfactant: An in vitro Study," Acta Paediatr. 90:412-416 (2001); Enhorning et al., "Phospholipases Introduced into the Hypophase Affect the Surfactant Film Outlining a Bubble," J Appl Physiol 73:941-945 (1992); Holm et al., "Inhibition of Pulmonary Surfactant by Phospholipases," J Appl Physiol 71:317-321 (1991); Duncan et al., "Susceptibility of Exogenous Surfactant to Phospholipase A$_2$ Degradation," Can J Physiol Pharmacol 74:957-963 (1996); Arbibe et al., "Generation of Lyso-Phospholipids From Surfactant in Acute Lung Injury is Mediated by Type II Phospholipase A$_2$ and Inhibited by a Direct Surfactant Protein A-Phospholipase A$_2$ Interaction," J Clin Invest 102:1152-1160 (1998), each of which is hereby incorporated by reference in its entirety). PLA$_2$ not only can degrade and deplete active surfactant glycerophospholipids, but also produces reaction byproducts such as lysophosphatidylcholine (LPC) and unsaturated free fatty acids that interact biophysically with intact surfactant to further impair surface activity (Holm et al., "Multiple Mechanisms of Lung Surfactant Inhibition," Pediatr Res 46:85-93 (1999); Wang et al., "Additivity of Protein and Non-protein Inhibitors of Lung Surfactant Activity," Am J Respir Crit. Care Med 158:28-35 (1998); Hall et al., "Inhibition of Pulmonary Surfactant by Oleic Acid: Mechanisms and Characteristics," J Appl Physiol 72:1708-1716 (1992), each of which is hereby incorporated by reference in its entirety). LPC and excess amounts of unsaturated free fatty acids can also directly injure the alveolocapillary membrane and increase its permeability to worsen pulmonary edema (Niewoehner et al., "Injurious Effects of Lysophosphatidylcholine on Barrier Properties of Alveolar Epithelium," J Appl Physiol 63:1979-1986 (1987); Hall et al., "Altered Function of Pulmonary Surfactant in Fatty Acid Lung Injury," J Appl Physiol 69:1143-1149 (1990), each of which is hereby incorporated by reference in its entirety).

In addition to phospholipase resistance, molecular changes in lipid analogs vary the hydrophobicity, molecular flexibility, functional cross-section, bilayer behavior, and surface activity of these compounds. The C16:0 moieties in selected analog compounds in analogy with DPPC (the most prevalent glycerophospholipid in endogenous lung surfactant) promote their ability to form tightly-packed surface films that generate very low surface tensions under dynamic compression.

At the same time, the use of ether or sulfur or other linkages instead of the 'normal' ester linkage between the fatty chains and the glycerol backbone enhances the adsorption and film respreading of analog compounds relative to DPPC. For example, ether linkages increase chain mobility and facilitate film respreading during cycling in the C16:0 diether analog compound DEPN-8 compared to DPPC (Turcotte et al., "Chemical Synthesis and Surface Properties of an Analog of the Pulmonary Surfactant Dipalmitoyl Phosphatidylcholine Analog," *Biochim Biophys Acta* 488:235-248 (1977); Liu et al., "Dynamic Interfacial Properties of Surface-Excess Films of Phospholipids and Phosphonolipid Analogs: I. Effects of pH," *J Colloid Interface Sci* 167:378-390 (1994); Liu et al., "Dynamic Interfacial Properties of Surface-Excess Films of Phospholipid and Phosphonolipid Analogs: II. Effects of Chain Linkage and Headgroup Structure," *J Colloid Interface Sci* 167:391-400 (1994), each of which is hereby incorporated by reference in its entirety). DEPN-8 is also able to form interdigitated as well as normal opposed bilayers (Skita et al., "Bilayer Characteristics of a Diether Phosphonolipid Analog of the Major Lung Surfactant Glycerophospholipid Dipalmitoyl Phosphatidylcholine," *J Lipid Res* 36:1116-1127 (1995), which is hereby incorporated by reference in its entirety), which further modifies its behavior in films and in lipid aggregates in the aqueous phase. The S and $SO_2$ linkages at the chain-backbone in selected analog compounds were chosen in part because sulfur is more hydrophobic than oxygen, and the use of sulfur-containing linkages maintains resistance to $PLA_1$ and $PLA_2$ as is the case with ether linkages. In addition, the headgroup analogy to phosphatidylglycerol (PG), utilized in some analog compounds of the present invention, was chosen because PG is a primary class of anionic glycerophospholipids in endogenous lung surfactant and has specific interactions with lung surfactant proteins (Notter, *Lung Surfactants: Basic Science and Clinical Applications*, Marcel Dekker, Inc, New York (2000)), which is hereby incorporated by reference in its entirety). In particular, the PG-related lipid analogs of the present invention are designed to facilitate interactions with the positive charges present in the headgroup of choline-related analogs and/or with positively charged amino acid residues present in synthetic peptides.

317 (2001), which is hereby incorporated by reference in its entirety). Helical segments, and turn/disordered segments are identified.

Figure 10:
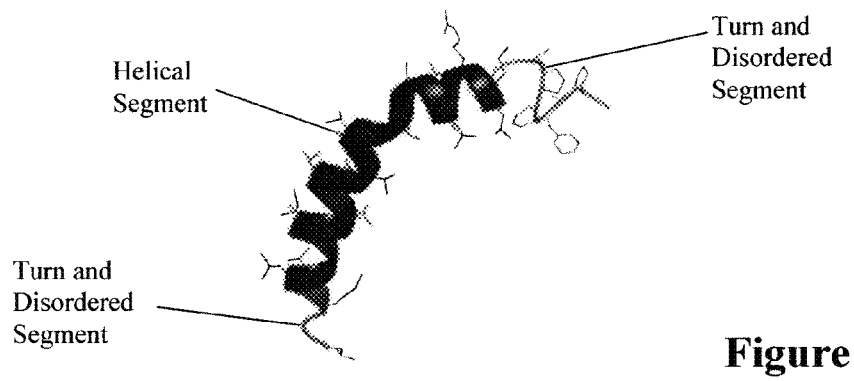

FIG. 10 illustrates the SP-Cff_Pro20 peptide structure of SEQ ID NO: 23 based on homology-templating of the SP-Cff sequence onto SP-C pig structure backbone (PDB) and substituting a proline at position 20 to inhibit the formation of non-functional structure (e.g., amyloid-like structure) followed by 1 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, and turn/disordered segments are identified.

Figure 11:
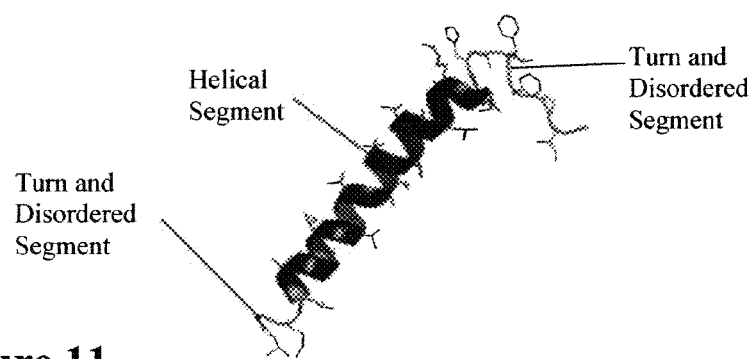

FIG. 11 illustrates the SP-C (FF) Pro24 peptide structure of SEQ ID NO: 24 based on homology-templating of the SP-Cff sequence onto SP-C pig structure backbone (PDB) and substituting a proline at position 24 to inhibit the formation of non-functional structure (e.g., amyloid-like structure) followed by 1 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, and turn/disordered segments are identified.

Figure 12:
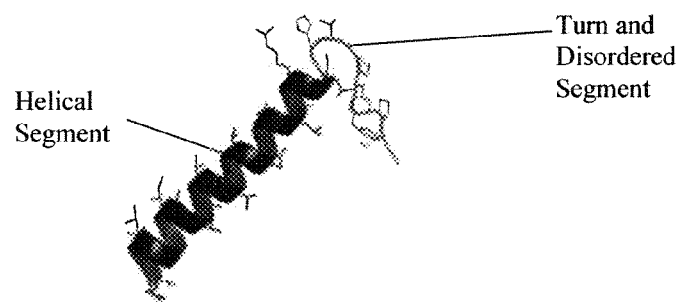

FIG. 12 illustrates the SP-Cff Pro28 peptide structure of SEQ ID NO: 25 based on homology-templating of the SP-Cff sequence onto SP-C pig structure backbone (PDB) and substituting a proline at position 28 to inhibit the formation of non-functional structure (e.g., amyloid-like structure) followed by 1 nsec dynamics simulation in methanol using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, and turn/disordered segments are identified.

FIG. 13 illustrates the structure of the stable covalent Lys17-Cys17 Mini-B dimer that includes two monomer units of SEQ ID NO: 12. The Lys-Cys derivative at position 17 was substituted into the loop domain of Mini-B to generate a novel stable covalent dimer having the capability of interacting with approximately twice the number of lipid molecules relative to the monomer. The structure shown for the Lys17-Cys17 Mini-B dimer is based on homology templating on two Mini-B monomer units (PDB 1SSZ) followed by 10 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified.

FIG. 14 illustrates the Super-Mini-B helix hairpin peptide structure of SEQ ID NO: 13 based on homology templating on to the structure of Mini-B (PDB) enhanced by the novel inclusion of a leader sequence made up of N-terminal residues 1-7 from human SP-B to increase the affinity of the full construct for lipids and lipid analogs, followed by 10 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified.

FIG. 15 illustrates the Super-Mini-B helix hairpin peptide dimer structure of SEQ ID NO: 14 based on homology templating onto the structure of Mini-B (PDB) enhanced by the novel inclusion of a leader sequence made up of N-terminal residues 1-7 from human SP-B to increase affinity for lipids and lipid analogs, plus added covalently-linked stable dimerization facilitated by the substitution of a Cys for Ile 3 of each Super Mini-B monomer to allow intermolecular disulfide linkage for the dimer. (A Cys for Phe 1 substitution presented in SEQ ID NO: 15 also allows intermolecular disulfide linkage for the dimer.) The structure shown for dimer Super Mini-B was derived using ZDOCK (Chen et al., "ZDOCK: An Initial-Stage Protein-Docking Algorithm", *PROTEINS: Structure, Function and Genetics* 52:80-87 (2003), which is hereby incorporated by reference in its entirety) based on disulfide linking of proximal Cys residues (Cys 3 illustrated) followed by 10 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified.

FIG. 16 illustrates the structure of Super Maxi-B (SEQ ID NO: 18) using the theoretical structure of bovine SP-B monomer (PDB 2IP3) as a template and Modeler version 7v6 (available online from the SalI lab; SalI et al., "Comparative Protein Modeling by Satisfaction of Spatial Restraints," *J. Mol. Biol.* 234:779-815 (1993), which is hereby incorporated by reference in its entirety), followed by 10 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Super Maxi B incorporates an N-terminal insertion sequence (Phe-Pro-Ile-Pro-Leu-Pro-Tyr) added onto Maxi-B (SEQ ID NO: 16) to enhance the ability of the Super Maxi-B peptide to interact with lipids, and also to provide the potential for additional non-covalent connectivity by pairing with other Super Maxi B peptides in an intermolecular hydrogen bonded beta sheet. The Ala residue at position 41 of Maxi-B is also mutated to Tyr in Super Maxi-B (position 48) to enhance the self-association of peptide monomer units into a non-covalent homo-dimer. Helical segments, disulfide linkages, and turn/disordered segments are identified. The Tyr 48 residue is also identified.

DETAILED DESCRIPTION OF THE INVENTION

The present invention relates to synthetic lung surfactant compositions that contain one or more of phospholipase-resistant phospho-glycerol derivatives, phospholipase-resistant phospho-choline derivatives, and surface active proteins or peptides, more preferably a combination of at least two or all three of these materials. Novel phospholipase-resistant phospho-glycerol derivatives, phospholipase-resistant phospho-choline derivatives, and surface active peptides are also disclosed herein.

As used herein, the term "phospholipase-resistant phospho-glycerol derivative" refers to a derivative of naturally occurring phospho-glycerol molecules in lung surfactant, where the derivative is resistant to one or more of phospholipases $A_1$, $A_2$, C, and D, and has a structural modification in one or more of the fatty acid chain-backbone linkage group (e.g., ether, thioether, etc.), phospho group, or the remainder of the head group including the glycerol group.

The phospholipase-resistant phospho-glycerol derivative is preferably a compound having a structure according to formulae (Ia) or (Ib)

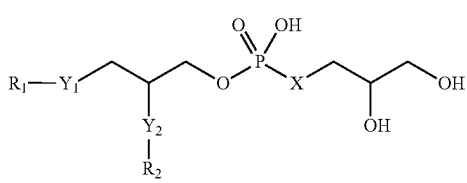
(Ia)

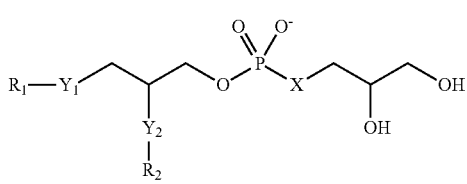
(Ib)

where X is O or $(CH_2)_n$ where n is an integer from 0 to 5, $Y_1$ and $Y_2$ are independently O, S, or $SO_2$; and $R_1$ and $R_2$ are independently C8-C24 hydrocarbons.

The hydrocarbon groups of $R_1$ and $R_2$ can be the same or different, and can be saturated, monounsaturated, or polyunsaturated hydrocarbons, although saturated and monounsaturated are preferred. Preferred hydrocarbons are C10-C22 hydrocarbons, more preferably C12-C20 hydrocarbons, most preferably C14-C18 hydrocarbons. According to one embodiment, the phospholipase-resistant phospho-glycerol derivative has a saturated $R_1$ group and a monounsaturated or polyunsaturated $R_2$ group.

When X is $(CH_2)_n$, n is preferably an integer from 0 to 2. The molecular change at the level of the phosphate group in phosphono-lipid analogs is believed to confer structural resistance to Phospholipase D.

The $Y_1$ and $Y_2$ linker groups can be the same or different. According to one preferred embodiment, at least one of these linker groups is S or $SO_2$, more preferably the $Y_1$ group. According to another embodiment, both $Y_1$ and $Y_2$ are S or $SO_2$. According to a further embodiment, both $Y_1$ and $Y_2$ are O. The synthetic lipids of the present invention are designed to have several important molecular features. One such feature is the molecular modifications used in the $Y_1$ and $Y_2$ linkage groups between the fatty chains and the glycerol backbone, which confer structural resistance to phospholipase $A_1$ ($PLA_1$) and $A_2$ ($PLA_2$).

According to one embodiment, the phospholipase-resistant phospho-glycerol derivative has the structure according to formula (Ib) and is present in the form of a salt, preferably a pharmaceutically acceptable salt. The term "pharmaceutically acceptable salt" refers to those salts that retain the biological effectiveness and properties of the free bases. The salts are formed with any suitable cation including, without limitation, sodium, potassium, calcium, magnesium, zinc, and protonated amino acid residues. Other salts are known to those of skill in the art and can readily be adapted for use in accordance with the present invention.

Exemplary phospholipase-resistant phospho-glycerol derivatives include, without limitation, 2,3-bis(hexadecyloxy)propyl 2,3-dihydroxypropyl hydrogen phosphate ("PG-A"); 2-((Z)-hexadec-9-enyloxy)-3-(hexadecyloxy) propyl 2,3-dihydroxypropyl hydrogen phosphate ("PG-B"); 2,3-bis(hexadecyloxy)propyl hydrogen 3,4-dihydroxybutyl-phosphonate ("PG-C"); 2-(hexadecyloxy)-3-(hexadecylthio)propyl 2,3-dihydroxypropyl hydrogen phosphate; 2-(hexadecyloxy)-3-(hexadecylsulfonyl)propyl 2,3-dihydroxypropyl hydrogen phosphate; 2-((E)-hexadec-9-enyloxy)-3-(hexadecylthio)propyl 2,3-dihydroxypropyl hydrogen phosphate; 2-((E)-hexadec-9-enyloxy)-3-(hexadecylsulfonyl)propyl 2,3-dihydroxypropyl hydrogen phosphate; 2-(hexadecyloxy)-3-(hexadecylthio)propyl hydrogen 3,4-dihydroxybutylphosphonate; 2-(hexadecyloxy)-3-(hexadecylsulfonyl)propyl hydrogen 3,4-dihydroxybutylphosphonate; 2-((E)-hexadec-9-enyloxy)-3-(hexadecylthio)propyl hydrogen 3,4-dihydroxybutylphosphonate; 2-((E)-hexadec-9-enyloxy)-3-(hexadecylsulfonyl)propyl hydrogen 3,4-dihydroxybutylphosphonate.

1,2-Dihexadecylglycerol and 1-hexadecyl-2-hexadec-9-encylglcerol can be prepared as describe previously (Wang et al., "Surface Activity of a Synthetic Lung Surfactant Containing a Phospholipase-Resistant Phosphonolipid Analog of Dipalmitoyl Phosphatidylcholine," *J. Physiol. Lung Cell Mol. Physiol.* 285:L550-L559 (2003); Chang et al., "Surface Properties of Sulfur- and Ether-Linked Phosphonolipids With and Without Purified Hydrophobic Lung Surfactant Proteins," *Chem Phys Lipids* 137:77-93 (2005); Harlos et al., "Influence of Calcium on Phosphatidylglycerol: Two Separate Lamellar Structures," *Biochemistry* 19:895-899 (1980), each of which is hereby incorporated by reference in its entirety). As shown in Scheme 1a below, this includes treating the starting material, a 1,2-disubstitutedglycerol, with phosphorous oxychloride and base to form the intermediate 1,2-disubstitutedglycerol phosphorus acid dichloride. The intermediate dichloride can be treated with solketal (1,2-isopropylideneglycerol). Removal of the isopropylidene protecting group can be achieved through treatment with 70:30 (v/v) acetic acid:water. The lipids can be isolated after extraction and column chromatography.

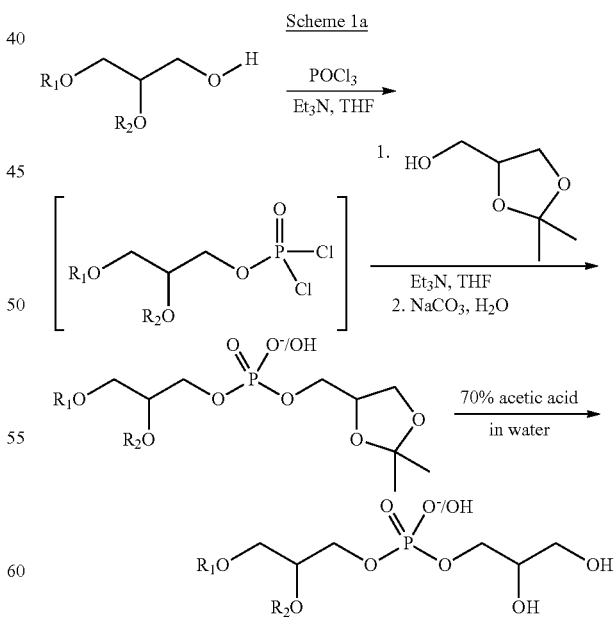

Scheme 1a

Various other phospholipase-resistant phospho-glycerol derivatives can be synthesized in this manner by using 1,2-disubstituted glycerols having the various $R_1$ and $R_2$ groups as defined above.

Phospholipase-resistant phospho-glycerol derivatives having an S linkage group $Y_2$ can be prepared by an alternative tactic, as illustrated in Scheme 1b below. The protocol entails chemistry based on the protocol reported by (Fuji et al., "A Stereoselective and Highly Practical Synthesis of Cytosolic Phospholipase A2 Substrate, 2-S-Arachidonoyl-1-O-hexadecyl-sn-2-thioglycero-3-O-phosphocholine," *J. Org. Chem.* 62:6804-6809 (1997), which is hereby incorporated by reference in its entirety). Trityl protected glycidol can react with a fatty alkyl alcohol or thiol to make oxirane ring-opened alcohol E, where $Y_1$=O or S. At this stage, the S can be converted to $SO_2$, through an oxidation reaction, if required. For eventual incorporation of the sulfur at the 2 position (i.e., $Y_2$=S), the alcohol of E is transformed to the p-nitrotoluenesulfonate ester (F), which is rapidly reacted with potassium thioacetate to make thiolacetate G. $LiAlH_4$ treatment affords thiol H and the trityl group is migrated from the oxygen to the sulfur through the use of $BF_3.Et_2O$. At this stage the protected phosphorus headgroup can be introduced on the alcohol of I, by carrying out the same chemistry (through J to K) as presented in Scheme 1b. Detritylation of K is achieved with the combination of silver nitrate in pyridine followed by hydrogen sulfide in pyridine. Formation of L is completed by alkylation of the free thiol using base and a fatty alkyl bromide. Phosphoglycerol formation is completed by deacetalization of L using 70% acetic acid in water.

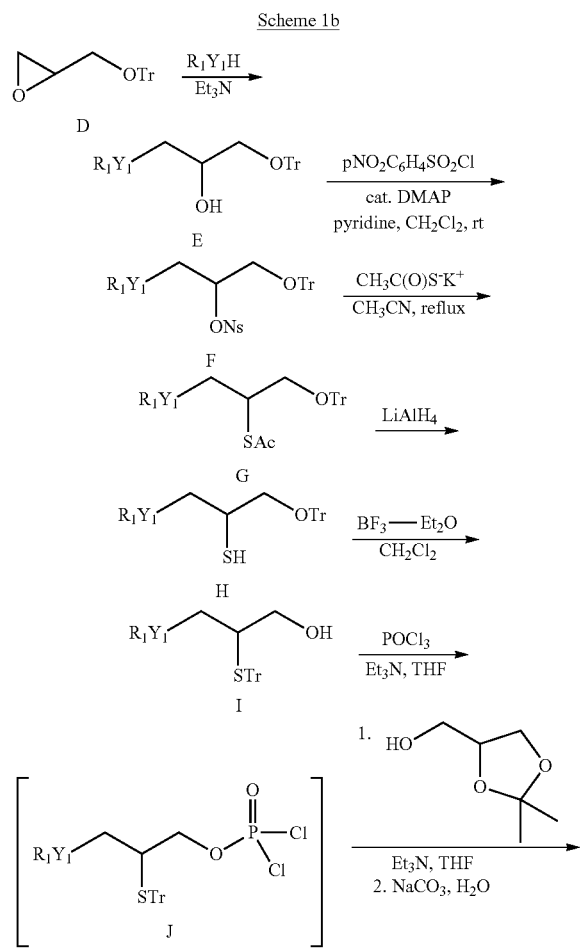

Scheme 1b

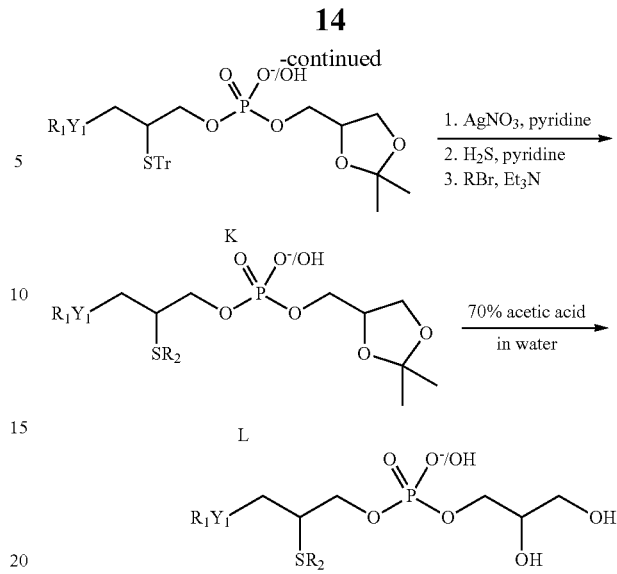

Phospholipase-resistant phosphonoglycerols can be prepared according to Scheme 2 illustrated below. The first two steps follow the literature (see Bittman et al., "Isosteric Phosphonate Analogs of ET-16-OMe. Synthesis and Biological Evaluation of the Enantiomers of 2'-(Trimethylammonio)ethyl 4-(hexadecyloxy)-3-methoxybutanephosphonate and 2'-(trimethylammonio)ethyl 4-(hexadecylthio)-3-methoxybutanephosphonate," *J. Med. Chem.* 37:425-430 (1994), which is hereby incorporated by reference in its entirety). The reaction of the lithium anion of dimethyl methanephosphonate and O-benzoylated glycidol (R) brings about attack opposite the ring substituent affording adduct S. The next step is a standard acylation of an alcohol to afford compound T. At this stage, the phosphorus containing unit of compound T can be adapted and the fatty glycerol component introduced. (As shown, $R_1$ and $R_2$ are identified as $C_{16}H_{33}$ groups within the structure of the fatty glycerol; it should be appreciated that these are merely exemplary.) This is done by first converting the dimethyl ester to a bis(trimethylsilyl) phosphonate (U). Compound U can then be converted to the dichloride which in turn reacts with the fatty alkyl substituted glycerol to afford the doubly benzoyl protected phosphonic acid V. The conversion to dichloride can be achieved with oxalyl chloride (see Bhongle et al., "Expedient and High-yield Synthesis of Alkylphosphonyl Dichlorides under Mild, Neutral Conditions: Reaction of bis(trimethylsilyl)alkyl phosphonates with oxalyl chloride/dimethylformamide," *Synth. Commun.* 17:1071-1076 (1987), which is hereby incorporated by reference in its entirety) or with phosphorus trichloride (Morita et al., "A Mild and Facile Synthesis of Alkyl- and Alkylphosphonyl Dichlorides under Neutral Conditions. Reaction of bis(trimethylsilyl) phosphonates with Phosphorus(V) Chloride," *Chem. Lett.* pp. 435-438 (1980), which is hereby incorporated by reference in its entirety). The final step of the lipid synthesis involves removal of the benzoyl protecting groups. This was done using a methanolysis of the benzoate under basic condition, which frees the hydroxy groups. It should be appreciated that any other protecting groups can be used, including without limitation of alkyl-O, trialkylsilyl-O, substituted benzyl-O, chloride, bromide, fluoride, acetate, pivaloate, trifluoroacetate, arenesulfonate, alkanesulfonate, and perfluorinated alkanesulfonate.

Scheme 2

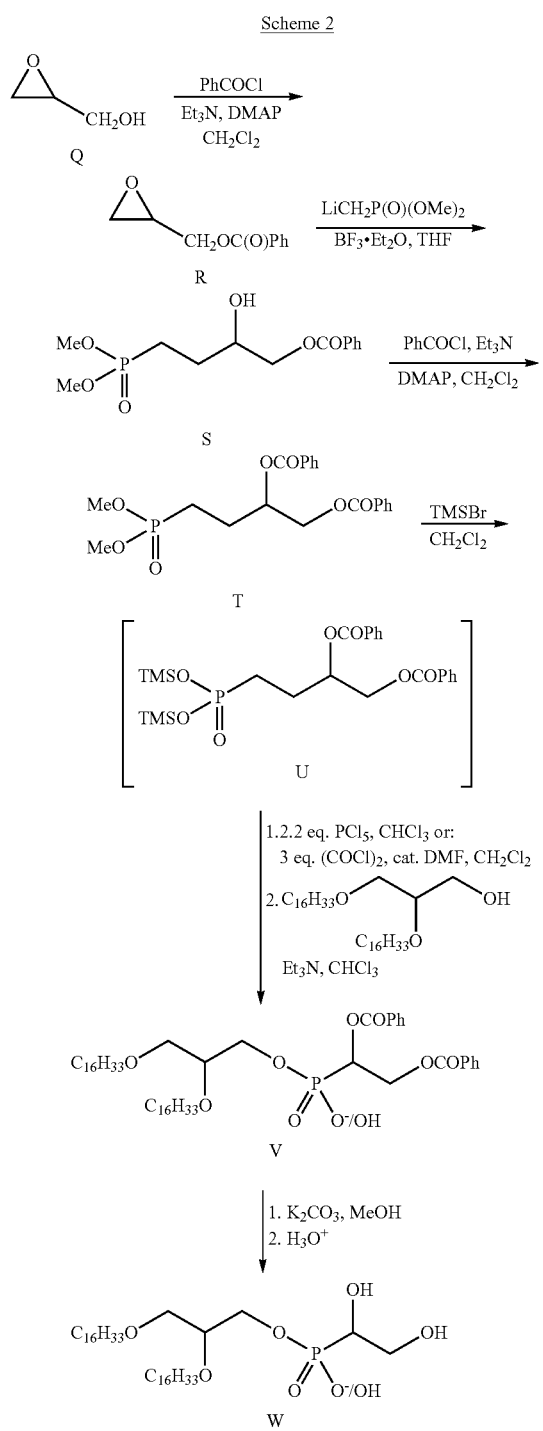

Scheme 3

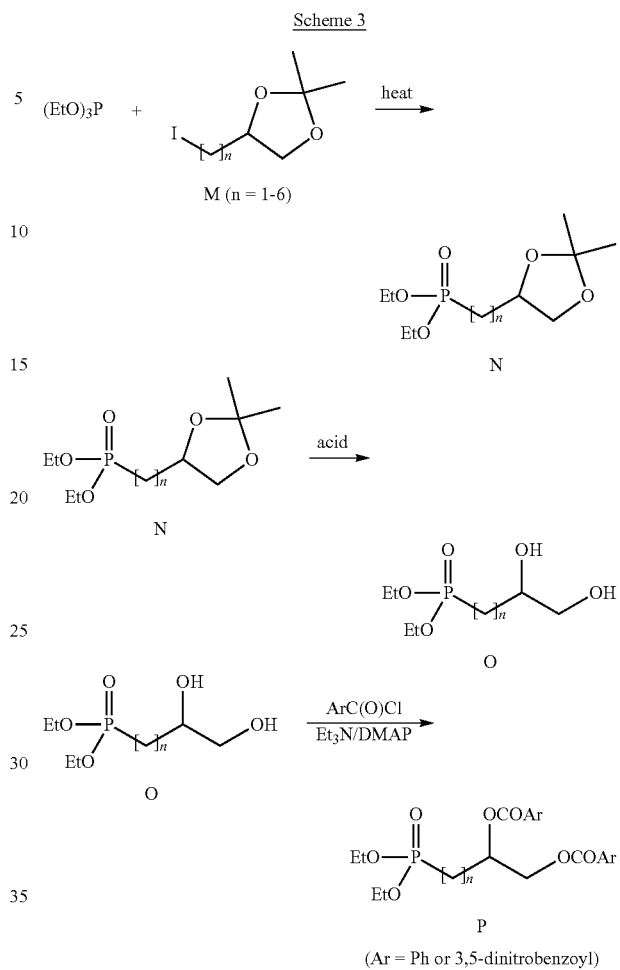

(Ar = Ph or 3,5-dinitrobenzoyl)

An alternative method of formation of phosphonodiols, which can be used in place of compound T in Scheme 2, is the Michaelis-Arbuzov reaction of triethyl phosphite on an alkyl iodide (M), already containing the acetal protected diol functionality within it. This is illustrated in Scheme 3 below. Typical deprotection was then executed, offering a free diol (O). Protecting groups (e.g., benzoyl) that are inert to the phosphorus manipulations need to be installed. Both alcohols had to be functionalized and this was done under typical conditions of benzoyl chloride and base.

Other synthesis protocols, whether known or subsequently developed, can also be used to prepare the phospholipase-resistant phospho-glycerol derivatives of the present invention.

As used herein, the term "phospholipase-resistant phospho-choline derivatives" refers to a derivative of naturally occurring phospho-choline molecules in lung surfactant, where the derivatives are resistant to one or more of phospholipases $A_1$, $A_2$, C, and D, and have a structural modification in one or more of the fatty acid chain-backbone linkage group (e.g., ether, thioether, etc.), phospho group, or the remainder of the head group including the choline group.

The phospholipase-resistant phospho-choline derivative preferably has a structure according to formula (II)

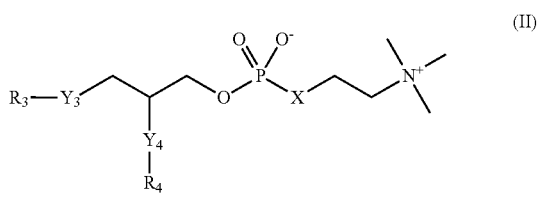

where X is O or $(CH_2)_n$ where n is an integer from 0 to 5, $Y_3$ and $Y_4$ are independently O, S, or $SO_2$, and $R_3$ and $R_4$ are independently C8-C24 hydrocarbons.

The hydrocarbon groups of $R_3$ and $R_4$ can be the same or different, and can be saturated, monounsaturated, or polyunsaturated hydrocarbons, although saturated and monounsaturated are preferred. Preferred hydrocarbons are C10-C22 hydrocarbons, more preferably C12-C20 hydrocarbons, most preferably C14-C18 hydrocarbons. According to one embodiment, the phospholipase-resistant phospho-glycerol derivative has a saturated $R_3$ group and a monounsaturated or polyunsaturated $R_4$ group.

When X is $(CH_2)_n$, n is preferably an integer from 0 to 2.

The $Y_3$ and $Y_4$ linker groups can be the same or different. According to one preferred embodiment, at least one of these linker groups is S or $SO_2$, more preferably the $Y_3$ group. According to another embodiment, both $Y_3$ and $Y_4$ are S or $SO_2$. According to a further embodiment, both $Y_3$ and $Y_4$ are O.

Exemplary phospholipase-resistant phospho-choline derivatives include, without limitation, [(±)-trimethyl(3-phosphonopropyl)ammonium, mono(2,3-bis(hexadecyloxy) propyl ester] ("DEPN-8"); [(±)-trimethyl(3-phosphonopropyl)ammonium, mono(2-hexadec-9-enyloxy-3-hexadecyloxypropyl) ester] ("UnDEPN-8"); [(±)-trimethyl (3-phosphonopropyl)ammonium, mono(2-hexadecyloxy-3-hexadecylsulfanylpropyl) ester] ("S-lipid"); [(±)-trimethyl (3-phosphonopropyl)ammonium, mono(2-hexadecyloxy-3-hexadecylsulfonylpropyl) ester] ("$SO_2$-lipid"); and combinations thereof. Of these phospholipase-resistant phospho-choline derivatives, DEPN-8 and $SO_2$-lipid are preferred.

The synthesis of several phospholipase-resistant phospho-choline derivatives, including DEPN-8, have been reported previously (see Turcotte et al., "Chemical Synthesis and Surface Activity of Lung Surfactant Phospholipid Analogs. II. Racemic N-Substituted Diether Phosphonolipids," *Biochim Biophys Acta* 1084:1-12 (1991); Turcotte et al., "Chemical Synthesis and Surface Properties of an Analog of the Pulmonary Surfactant Dipalmitoyl Phosphatidylcholine Analog," *Biochim Biophys Acta* 488:235-248 (1977); Liu et al., "Dynamic Interfacial Properties of Surface-Excess Films of Phospholipids and Phosphonolipid Analogs. I. Effects of pH," *J Colloid Interface Sci* 167:378-390 (1994); Liu et al., "Dynamic Interfacial Properties of Surface-Excess Films of Phospholipid and Phosphonolipid Analogs: II. Effects of Chain Linkage and Headgroup Structure," *J Colloid Interface Sci* 167:391-400 (1994); Liu et al., "Thermotropic Behavior of Structurally-Related Phospholipids and Phosphonolipid Analogs of Lung Surfactant Glycerophospholipids," *Langmuir* 11:101-107 (1995); Wang et al., "Surface Activity of a Synthetic Lung Surfactant Containing a Phospholipase-Resistant Phosphonolipid Analog of Dipalmitoyl Phosphatidylcholine," *Am J Physiol* 285:L550-L559 (2003); Chang et al., "Surface Properties of Sulfur- and Ether-Linked Phosphonolipids With and Without Purified Hydrophobic Lung Surfactant Proteins," *Chem Phys Lipids* 137:77-93 (2005), each of which is hereby incorporated by reference in its entirety). Other modifications to the synthesis procedures previously described can be made to achieve phospholipase-resistant phospho-choline derivatives that possess alternative $Y_3$ and $Y_4$ group configurations. These include the procedures described above for synthesis of phospholipase-resistant phospho-glycerol derivatives that possess S or $SO_2$ for both $Y_1$ and $Y_2$.

The phospholipase-resistant lipid compounds of the present invention can be present in the form of a racemic mixture, containing substantially equivalent amounts of stereoisomers. In another embodiment, the compounds of the present invention can be prepared or otherwise isolated, using known procedures, to obtain a single stereoisomer substantially free of its corresponding stereoisomer (i.e., substantially pure). By substantially pure, it is intended that a stereoisomer is at least about 95% pure, more preferably at least about 98% pure, most preferably at least about 99% pure. Both racemic mixtures and substantially pure stereoisomers of the phospholipase-resistant lipid compounds can be used to prepare surfactant compositions of the present invention.

The surface-active proteins or peptides can be one or more lung surfactant proteins (e.g., purified from lung tissue or from lung washings) (Notter, *Lung Surfactants: Basic Science and Clinical Applications*, Marcel Dekker, Inc, New York (2000)), one or more surface active synthetic peptides, or one or more surface-active peptidomimetic compounds. In an effort to prepare an entirely synthetic lung surfactant composition, use of one or more synthetic peptides or surface-active peptidomimetic compounds is preferred.

The term "surface-active synthetic peptide" is meant to include a synthetic peptide that increases the ability of the surfactant composition to lower surface tension during adsorption and/or during dynamic compression in a spread or adsorbed interfacial (surface) film. Preferred "surface-active synthetic peptides" are amphipathic or hydrophobic.

The surface-active synthetic peptides of the present invention have been designed to have optimal surface-active interactions with synthetic lipid analogs when present in surfactant compositions of the present invention. However, these peptides can also be used in combination with any phospholipids, whether they are phospholipase-resistant or not. Such phospholipids can include native phospholipids present in endogenous surfactant or commercially available exogenous surfactant preparations.

The surface-active synthetic peptides of this invention can be related in primary sequence to regions (or the full length) of surfactant proteins (SP)-A, SP-B, or SP-C, and may also incorporate added features such as homo- or hetero-dimerization. Particularly preferred amphipathic peptides for this invention are those related to the regional or full-length sequence of human or animal SP-B, including dimer forms, which may be used in synthetic lung surfactants with lipid analogs as single peptides or in combination with added synthetic peptides related to the regional or full sequence of SP-C or SP-A. These preferred peptides can also be combined in synthetic exogenous surfactants with 'regular' (e.g., ester-linked) synthetic phospholipids including those found in native lung surfactant. Also, a group of additional linear amphipathic peptides are also included here for combination with lipid analogs in synthetic exogenous surfactants.

The structural features of the full-length mature SP-A, SP-B, and SP-C proteins are well known and reported as Genbank Accession Nos. L10123, BC111570, BC111571, BC026229, NM_006926, and NM_005411 for SP-A; L11573, AF400074, BC032785, NM_000542, and NM_198843 for SP-B; and J03890, U02948, $AY_{357924}$, AY337315, BC005913, and NM_003018 for SP-C. Each of the above-listed Genbank Accessions is hereby incorporated by reference in its entirety.

When fragments of the mature SP-A, SP-B, and/or SP-C are employed in the surfactant compositions of the present invention, it is preferable to utilize fragments thereof that contain at least a portion of a lipid associating region. Lipid associating regions are those portions of the mature protein that are capable of molecular interaction with lipids (either native glycerophospholipids or synthetic phospholipase-resistant lipids) to promote surface activity of the resulting composition in which they are introduced. Such fragments include, without limitation, fragments of SP-A that contain an amphipathic or hydrophobic region capable of associating with lipids, fragments of SP-B that contain an amphipathic or hydrophobic region capable of associating with lipids, fragments of SP-C that contain an amphipathic or hydrophobic region capable of associating with lipids, as well as any number of synthetic peptides or combinations thereof.

Two important synthetic peptide families of the present invention have molecular features analogous to SP-B and are designed to include peptides that include the consensus of

```
                                            (SEQ ID NO: 1)
CXXCBXXXBBXBXXXPBXXBXXPBXXCBXXXBCB
``` where each X is any amino acid and each B is a hydrophilic residue (lysine, arginine, histidine, aspartic acid, glutamic acid); and peptides that include the consensus of

```
                                            (SEQ ID NO: 2)
CXXCBXXXBBXXXXXPBXXXXXXXXXXCBXXPXXXXXXCXZXX**BS
XXXXBBXXXBXXPXXXCBXXXBCB
``` where each B represents hydrophilic residues (lysine, arginine, histidine, aspartic acid, or glutamic acid), Z is sequence position specific for residues alanine, phenylalanine or tyrosine, "**" is sequence specific for residues glutamic acid-arginine or aspartic acid-lysine pairs for intermolecular salt-bridge formation; and each X represents more hydrophobic amino acids based on the Wimley and White hydrophobicity scale for amino acids in proteins that partition into octanol, lipids and membranes similar to hydrophobicity of surfactant lipid ensembles (Wimley and White, "Experimentally Determined Hydrophobicity Scale for Proteins at Membrane Interfaces," *Nat. Struct. Biol.* 3:842-848 (1996), which is hereby incorporated by reference in its entirety). These hydrophobic amino acids include hydrophobic (non-polar) residues (valine, isoleucine, leucine, methionine, phenylalanine, tryptophan, tyrosine, cysteine, glycine, alanine, proline, asparagine, glutamine, or serine).

A third peptide family of the present invention includes peptides that have molecular analogy to SP-C and include the consensus of

```
                                            (SEQ ID NO: 3)
FGIPXXPVHLKR[LLVVVVVVVLVVVVIVGALLM]GL
``` where P can be substituted for any one or multiples of the bracketed amino acids at positions 13-33, and/or X residues at positions 5 and 6 are phenylalanine or cysteine residues that are thioester-linked to palmitate or lysine residues that are amide-linked to palmitate.

In addition to being designed to promote lipid surface activity based on specific structural analogies with native SP, the synthetic peptides of this patent are also designed to include structural modifications to retard the transition of surface-active helical structures to extended amyloid-like structures that have attenuated surface activity and/or increased surface or shear viscosity (Gordon et al., "Conformational Mapping of the N-Terminal Peptide of HIV-1 gp41 in Lipid Detergent and Aqueous Environments Using $^{13}$C-Enhanced Fourier Transform Infrared Spectroscopy," *Protein Sci* 13:1012-1030 (2004), which is hereby incorporated by reference in its entirety).

Figure 3:
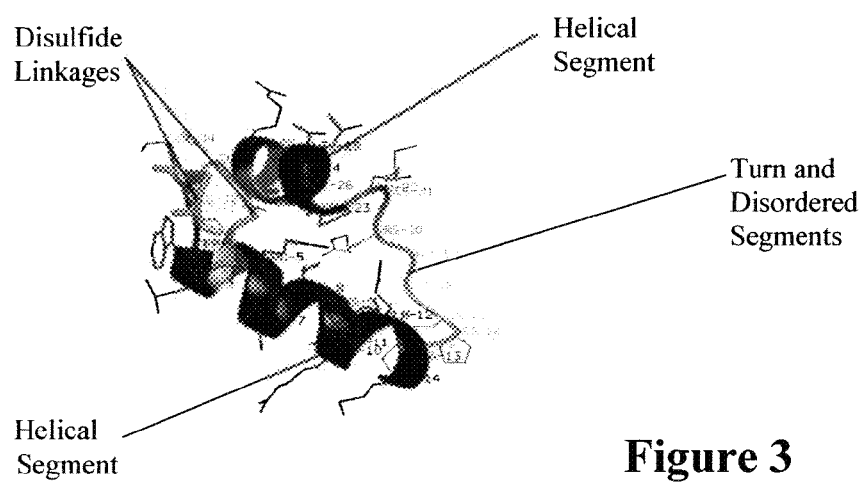
FIG. 3 illustrates the Mini-B peptide structure of SEQ ID NO: 4 (PDB accession code 1SSZ structure). Helical segments, disulfide linkages, and turn/disordered segments are identified.
Figure 4:
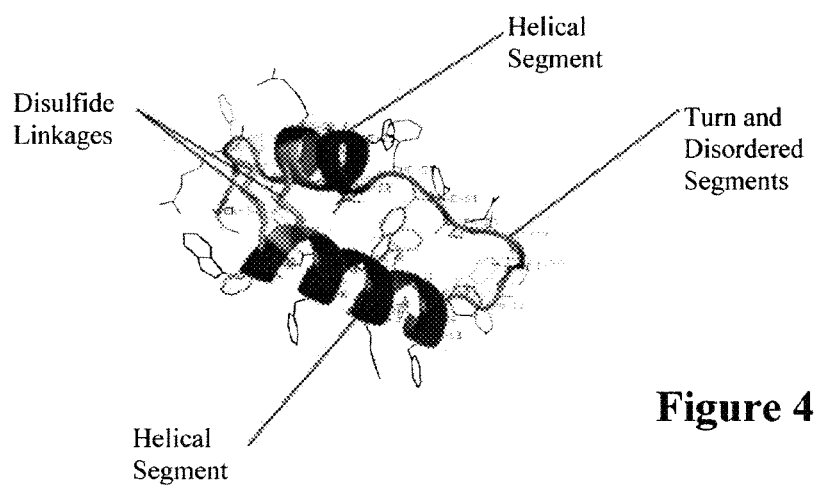
FIG. 4 illustrates the FK helix-hairpin peptide structure of SEQ ID NO: 5, which is based on homology-templating of the sequence onto the Mini-B backbone (structure PDB 1 SSZ) followed by 20 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified.
Figure 5:
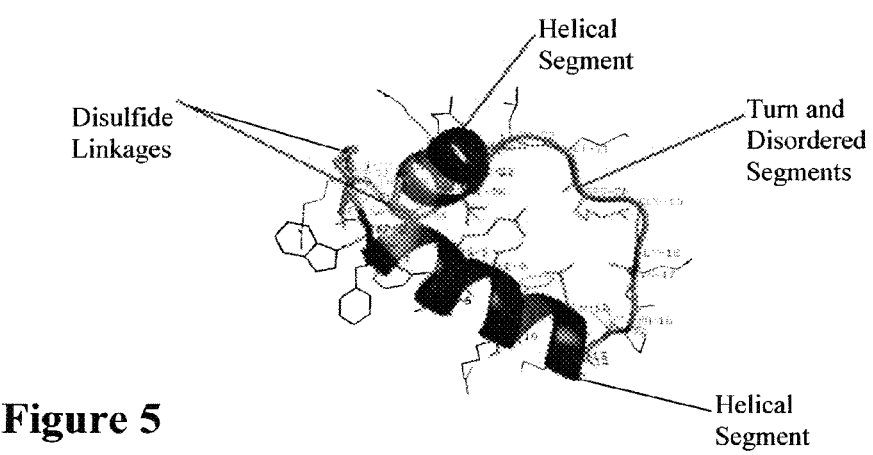
FIG. 5 illustrates the Mini-B Phe-N-term-helix peptide structure of SEQ ID NO: 6 based on homology-templating of the sequence onto the Mini-B backbone (structure PDB 1 SSZ) followed by 20 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified.

The peptide family corresponding to SEQ ID NO: 1 (designated "Mini-B family") incorporates functionally-relevant features of native SP-B, as templated on a highly active 34 amino acid SP-B mimic designated surfactant peptide Mini-B (Protein Data Bank Coordinate accession number 1 SSZ, which is hereby incorporated by reference in its entirety). Mini-B (SEQ ID NO: 4) has previously been shown to emulate some of the in vivo and in vitro surface activity of full length SP-B (Waring et al., "The Role of Charged Amphipathic Helices in the Structure and Function of Surfactant Protein B (SP-B)," *J Peptide Res* 66:364-374 (2005), which is hereby incorporated by reference in its entirety). Additional exemplary peptides in the Mini-B family that have structures according to consensus SEQ ID NO: 1 are specified in following paragraphs. These peptides incorporate key amphipathic helical elements of the N-terminal and C-terminal domains of SP-B in a stable Saposin protein fold format (e.g., a disulfide linkage between Cys-1 and Cys-33 and another disulfide linkage between Cys-4 and Cys-27), which is the same protein fold (helix-bend-helix stabilized by N-terminal/C-terminal disulfide connectivity) that occurs in native SP-B (see, e.g., FIGS. 3-5 showing the structure of SEQ ID NOS: 4-6, respectively). Alternatively, one or more of the Cys residues in such peptides can be reduced, or one of the Cys-based disulfide linkages replaced with hydrophobic residues, including but not limited to alanine or serine, to stabilize the structure in analogy with the action of the two intramolecular Cys-based disulfide linkages present in Mini-B. This tertiary fold not only captures many of the lipid-active elements of SP-B, but also stabilizes the structure in the helix-turn-helix hairpin conformation, helping the synthetic peptide to resist non-functional amyloid-like structure formation so as to maximize shelf life and/or improve viscosity behavior.

Exemplary peptides that correspond to the peptide of SEQ ID NO: 1 include, without limitation:

```
                                            SEQ ID NO: 4
CWLCRALIKRIQAMIPKGGRMLPQLVCRLVLRCS,

SEQ ID NO: 5
CWFCRFFFKRFFFFFPKGGRFFPFFFCRFFFRCS,

SEQ ID NO: 6
CWFCRAFIKRFQAMIPKGGRMLPQLVCRLVLRCS,

SEQ ID NO: 7
CWLCRALIKRIQAMIPKGGRMFPQFFCRFFFRCS,

SEQ ID NO: 8
CWFCRAFIKRFQAMIPKGGRMFPQFFCRFFFRCS,

SEQ ID NO: 9
CWFCRAFIKRFQAMIPKGERMLPQLVCRLVLRCS,

SEQ ID NO: 10
CWLCRALIKRIQAMIPKGERMFPQFFCRFFFRCS,

SEQ ID NO: 11
CWFCRAFIKRFQAMIPKGERMFPQFFCRFFFRCS,
``` and combinations thereof.

Three additional exemplary peptides that are related to consensus SEQ ID NO:1, but that also incorporate further novel modifications, are a stable covalently-linked Lys17-Cys17 Mini-B dimer (monomer units defined in SEQ ID NO: 12) that has the potential to interact biophysically with greater numbers of lipid molecules so as to increase surface activity relative to Mini-B; a 41 amino acid peptide designated as Super Mini-B (SEQ ID NO: 13) that incorporates an N-terminal leader sequence that significantly increases interactions and surface activity with lipids compared to Mini-B; and a covalently-linked Super Mini-B dimer (monomer units defined in SEQ ID NOS: 14 and/or 15) that has the potential to interact with increased numbers of lipid molecules compared to Super Mini-B.

The peptide designated as Mini-B dimer is composed of two monomer units that are modified from SEQ ID NO: 4 by the substitution of a Lys-Cys (K-C) derivative at position 17. Use of a K-C derivative to allow for disulfide linkage has been described in other peptides (see Alves et al., "Synthesis and Use of a Pseudo-cysteine for Native Chemical Ligation," J. Peptide Science 9:221-228 (2003), which is hereby incorporated by reference in its entirety). Thus, this K-C substitution at position 17 allows a disulfide linkage between Mini-B monomer units to yield a stable covalent Mini-B dimer (see FIG. 13). Each monomer unit in the Mini-B dimer peptide has the sequence:

SEQ ID NO: 12
CWLCRALIKRIQAMIPXGGRMLPQLVCRLVLRCS.

The Super Mini-B peptide has a primary sequence containing 41 amino acids that adds a 7 residue N-terminal leader sequence to Mini-B to give a peptide with a greater ability to insert into lipid layers (see FIG. 14). The Super Mini-B peptide has the amino acid sequence shown below:

SEQ ID NO: 13
FPIPLPYCWLCRALIKRIQAMIPKGGRMLPQLVCRLVLRCS.

The Super Mini-B dimer is composed of two monomer units, each containing a cysteine substituted for isoleucine at position 3 in the Super Mini-B sequence of SEQ ID NO: 13 to allow a disulfide linkage and the formation of a stable covalent dimer peptide (see FIG. 15). Each monomer unit in the Super Mini-B dimer peptide has the sequence:

SEQ ID NO: 14
FPCPLPYCWLCRALIKRIQAMIPKGGRMLPQLVCRLVLRCS
or

SEQ ID NO: 15
CPIPLPYCWLCRALIKRIQAMIPKGGRMLPQLVCRLVLRCS.

SEQ ID NO: 15 differs from SEQ ID NO: 14 in that the Phe1 residue rather than the Ile3 residue (of SEQ ID NO: 13) is replaced with Cys. The dimer can also be a hetero-dimer containing one monomer of each of SEQ ID NOS: 14 and 15.

Figure 6:
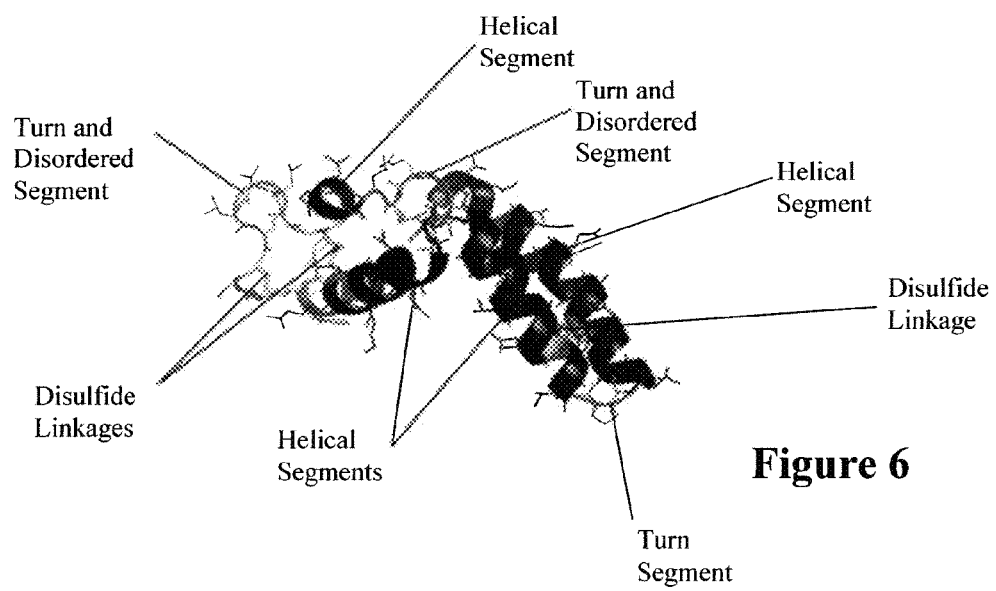
FIG. 6 illustrates the Maxi-B parent peptide structure of SEQ ID NO: 16 based on homology-templating of the SP-B sequence onto NK-lysin structure backbone (PDB) followed by 20 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified.
Figure 7:
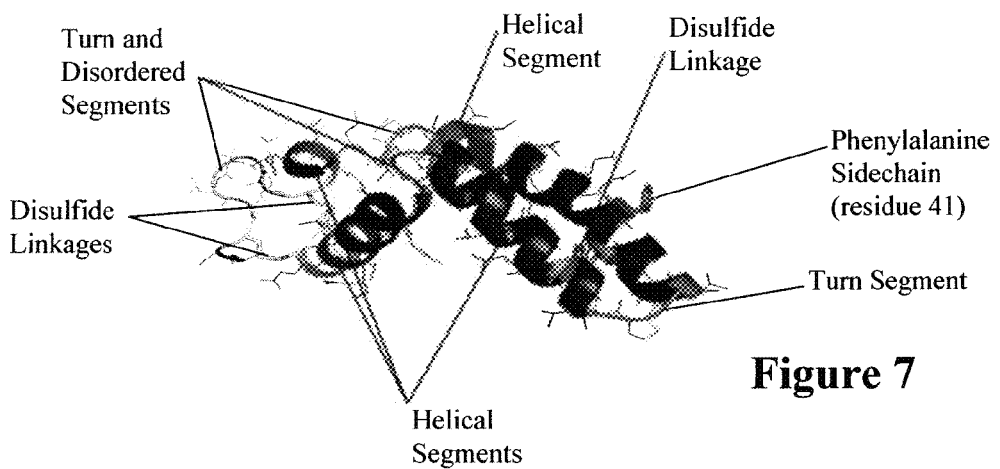
FIG. 7 illustrates the Maxi-B phe peptide structure of SEQ ID NO: 17 based on homology-templating of the SP-B sequence onto NK-lysin structure backbone (PDB) followed by 20 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, disulfide linkages, and turn/disordered segments are identified. The intermolecular interactive side chain of phenylalanine at position 41 is also identified.
Figure 8:
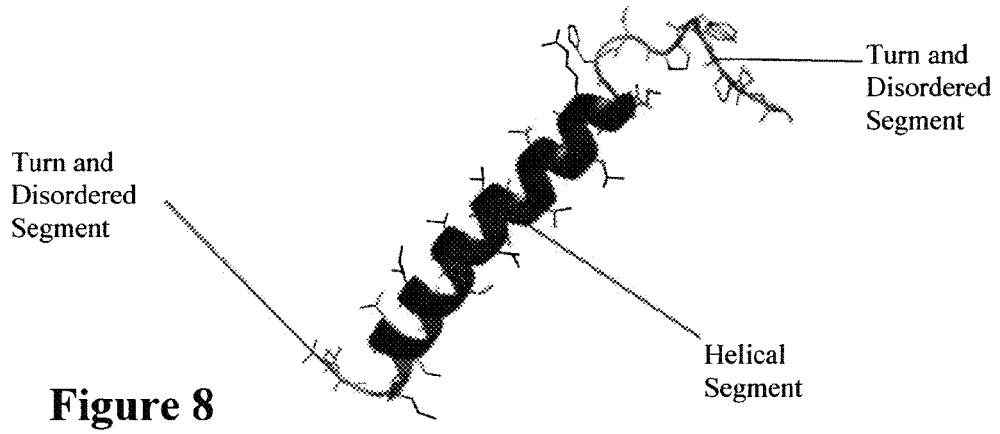
FIG. 8 illustrates the SP-Cff unsubstituted peptide structure of SEQ ID NO: 21 based on homology-templating of the SP-Cff sequence onto SP-C pig structure backbone (PDB) followed by 1 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments, and turn/disordered segments are identified.
Figure 9:
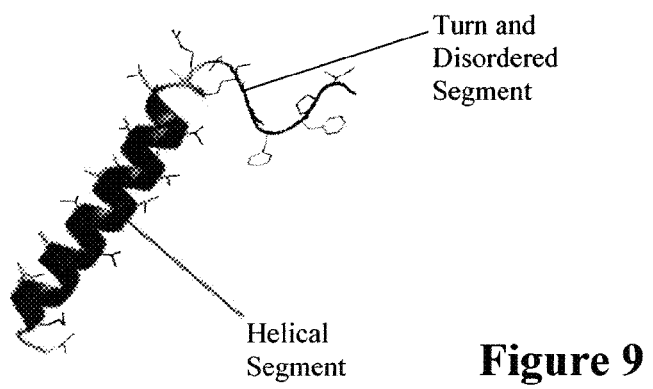
FIG. 9 illustrates the SP-Cff_Pro16 peptide structure of SEQ ID NO: 22 based on homology-templating of the SP-Cff sequence onto SP-C pig structure backbone (PDB) and substituting a proline at position 16 to inhibit the formation of non-functional structure (e.g., amyloid-like structure) followed by 1 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-

A second family of synthetic peptides in this application that are also related to SP-B contains compounds having the consensus of SEQ ID NO: 2 ("Maxi-B family"). This peptide family incorporates molecular interactions not present in shorter Mini-B family peptides (active native human SP-B has 78 amino acids in its monomeric form, while Mini-B and related peptides are substantially shorter). The Maxi-B family includes peptides with up to five amphipathic helices in helix hairpin format stabilized by disulfide linkages between cysteine residues at positions 1 and 70, positions 4 and 64, and positions 28 and 39. This peptide family contains molecular features designed to promote self-association as a homodimer in analogy with human SP-B, but without the disulfide linkage at cysteine residue 41 in the native protein, which is replaced with alanine, phenylalanine, or tyrosine in the maxi-B family. The latter two residues (F or Y) at position 41 afford additional stability by an aromatic ring stacking mechanism (Roe, "Conformation and Antimicrobial Activity of Linear Derivatives of Tachyplesin Lacking Disulfide Bonds," Arch. Biochem. and Biophys. 361:127-134 (1999), which is hereby incorporated by reference in its entirety) that forms a stable non-covalent ensemble that mimics a disulfide linkage between the two monomers to form a homodimer having monomeric orientations similar to native SP-B dimer. Homodimeric association in the Maxi-B family is also facilitated by a naturally-occurring intermolecular salt bridge at positions 44 and 45 where glutamic acid or aspartic acid, and arginine or lysine, constitute members of the salt bridge pair. The overall Maxi-B family also includes peptides where the disulfide linkage between Cys 1 and Cys 70 is retained, but the Cys residues at one or both of positions 4 and 64 is replaced with any hydrophobic (non-polar) residue that will stabilize the structure and retain activity. These Maxi-B family peptides also have the potential to participate in added in vivo activities carried out by native SP-B, i.e., metabolic or regulatory activities other than those directly involved in enhancing lipid surface activity. The Maxi-B peptide of SEQ ID NO: 16 (see FIG. 6) incorporates the majority of the primary sequence of native human SP-B, i.e., 91% homology including residues 8-78 of the native human protein. The Maxi-B peptide family in this application also includes Maxi-B phe (SEQ ID NO: 17), a variant of Maxi-B that has enhanced potential for self-association characteristics (see FIG. 7). Since the dominant molecular species of native SP-B is a covalently linked homo-dimer, the Maxi-B phe peptide is designed to promote dimeric self-association without the added synthesis costs that would apply if this were done chemically. A third exemplary peptide in the Maxi-B family is Super Maxi-B (SEQ ID NO: 18), which incorporates an N-terminal insertion sequence (Phe-Pro-Ile-Pro-Leu-Pro-Tyr) that is added onto the sequence of Maxi-B (SEQ ID NO: 16) to enhance the ability to insert and interact in lipid films and multilayers, and also provides the potential for further non-covalent connectivity by pairing with other Super Maxi B peptides in an intermolecular hydrogen bonded beta sheet (see FIG. 16). The Ala residue at position 41 of Maxi-B (SEQ ID NO: 16) is also mutated to Tyr at position 48 in Super Maxi-B (SEQ ID NO: 18) to enhance the self-association of peptide monomer units into a non-covalent homo-dimer. In addition, although some Maxi-B family peptides are designed for self-associated dimer formation, the Maxi-B family also includes covalent dimer peptides analogous to dimer Super Mini-B (SEQ ID NO: 14 and SEQ ID NO 15), where Phe 1 or Ile3 in the N-terminal insertion sequence of each Super Maxi-B monomer unit (SEQ ID NO: 18) is replaced with a Cys residue to allow a stable disulfide linkage to form a covalent Super Maxi-B dimer. These are presented as SEQ ID NOS: 19 and 20.

Exemplary peptides that correspond to the consensus of SEQ ID NO: 2 include, without limitation, SEQ ID NO: 16
CWLCRALIKRIQAMIPKGALAVAVAQVCRVVPLVAGGICQAL
AERYSVILLDTLLGRMLPQLVCRLVLRCS, SEQ ID NO: 17
CWLCRALIKRIQAMIPKGALAVAVAQVCRVVPLVAGGICQFLAE
RYSVILLDTLLGRMLPQLVCRLVLRCS, SEQ ID NO: 18
FPIPLPYCWLCRALIKRIQAMIPKGALAVAVAQVCRVVPLVVGGIC
QYLAERYSVILLDTLLGRMLPQLVCRLVLRCS,

```
                                         SEQ ID NO: 19
CPIPLPYCWLCRALIKRIQAMIPKGALAVAVAQVCRVVPLVVGGI
CQYLAERYSVILLDTLLGRMLPQLVCRLVLRCS,

SEQ ID NO: 20
FPCPLPYCWLCRALIKRIQAMIPKGALAVAVAQVCRVVPLVVGGI
CQYLAERYSVILLDTLLGRMLPQLVCRLVLRCS,
``` and combinations thereof.

A third family of peptides in this invention contains synthetic compounds that have structural analogy to human SP-C. Peptides in this SP-C variant family are according to the consensus of SEQ ID NO: 3 (Alonso et al., "Keeping Lung Surfactant Where It Belongs: Protein Regulation of Two-Dimensional Viscosity," *Biophysical J.* 89:266-273 (2005), which is hereby incorporated by reference in its entirety). These peptides have the novel feature of vicinal phenylalanine residues at positions 5 and 6 in the sequence, which may also be replaced with cysteine residues that are thioester-linked to palmitate or by lysine residues amide-linked to palmitate. SP-C variants in this family can also have a proline substituted for any one or more of the residues in the alpha helical region (see FIGS. 8-12 showing structures of SEQ ID NOS: 21-25, respectively).

Exemplary peptides that correspond to the peptide of SEQ ID NO: 3 include, without limitation,

```
FGIPFFPVHLKRLLVVVVVVVLVVVVIVGALLMGL,    SEQ ID NO: 21

FGIPFFPVHLKRLLVPVVVVVLVVVVIVGALLMGL,    SEQ ID NO: 22

FGIPFFPVHLKRLLVVVVVVPVLVVVVIVGALLMGL,   SEQ ID NO: 23

FGIPFFPVHLKRLLVVVVVVVLVPVVIVGALLMGL,    SEQ ID NO: 24

FGIPFFPVHLKRLLVVVVVVVLVVVVIPGALLMGL,    SEQ ID NO: 25
``` and combinations thereof.

A fourth family of amphipathic peptides of the present invention (that are intended for use with lipid analogs in synthetic lung surfactants) are linear amphipathic peptide sequences corresponding to the consensus of $$NH_2\text{-Phe}_a\text{-(Lys/Arg-Phe}_b)_c\text{-Xaa,}$$

where for each peptide Xaa is optional and can be Lys (K) or Arg (R), a is an integer that is 0 or 1, b is an integer that is from 1-8, and c is an integer that is from 3 to 20.

Each repeat of the (Lys/Arg-Phe$_b$)$_c$ group can be the same or different. Thus, Lys-Phe and Arg-Phe repeats can be present within the same peptide. Alternatively, the peptides contain only type one of the Lys-Phe or Arg-Phe repeats according to the structures $$NH_2\text{-Phe}_a\text{-(Lys-Phe}_b)_c\text{-Xaa and }NH_2\text{-Phe}_a\text{-(Arg-Phe}_b)_c\text{-Xaa}$$

where for each peptide Xaa is optional and can be Lys (K) or Arg (R), and a, b, and c are defined as listed above.

Figure 1:
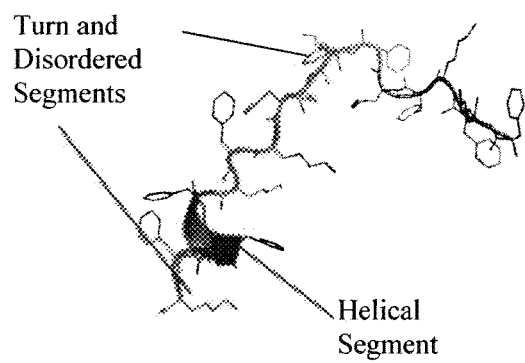
FIG. 1 illustrates the molecular modeling of SEQ ID NO: 26 (Poly-KF peptide structure) based on a starting structure of 100% alpha helix followed by 1 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments and turn/disordered segments are identified. This sequence forms some amphipathic helix, amphipathic beta sheet, and random conformations.
Figure 2:
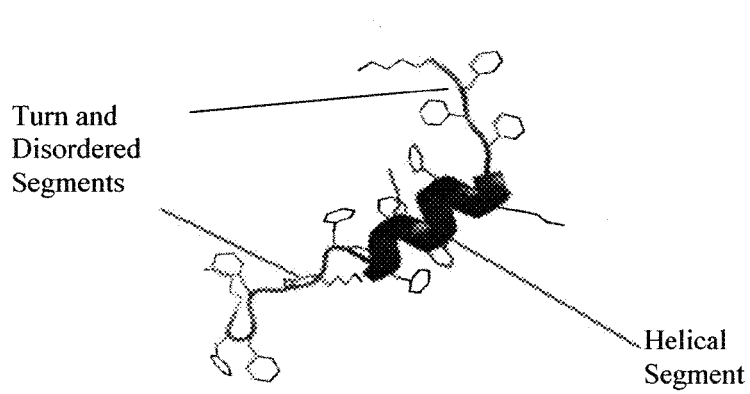
FIG. 2 illustrates the molecular modeling of SEQ ID NO: 27 ($F_4K$ peptide structure) based on an assumed starting structure of 100% alpha helix followed by 1 nsec dynamics simulation in methanol periodic box at 300° K using GROMACS force field (Lindahl, et al., "GROMACS 3.0: A Package For Molecular Simulation and Trajectory Analysis," *J. Mol. Mod.* 7:306-317 (2001), which is hereby incorporated by reference in its entirety). Helical segments and turn/disordered segments are identified. This peptide has a larger and more stable helical conformation than Poly-KF in FIG. 1.

These peptides form simple alpha helical structures in structure-promoting solvents such as methanol and in surfactant lipid dispersions in the aqueous phase (see, e.g., FIGS. 1 and 2 showing the structures of SEQ ID NOS: 26 and 27). When combined with synthetic lipids as described above, the synthetic surfactant composition exhibits surface activity that approaches that of the most active forms of native lung surfactant. Exemplary peptides of this family include, without limitation,

```
FKFKFKFKFKFKFKFKFKFK,     SEQ ID NO: 26

KFFFFKFFFFKFFFFKFFFFK,    SEQ ID NO: 27

FRFRFRFRFRFRFRFRFRFR,     SEQ ID NO: 28

RFFFFRFFFFRFFFFRFFFFR,    SEQ ID NO: 29

RFFFFKFFFFRFFFFRFFFFK,    SEQ ID NO: 30
``` and combinations thereof.

The synthetic peptides of the present invention are designed with amino acid sequences that retard the transition of helical structures to non-specific or amyloid-like structures. Without being bound by belief, it is believed the synthetic peptides will increase shelf life as well as reduce surface or shear viscosity in synthetic lung surfactants to improve their ease of pulmonary delivery. In addition, the synthetic peptides of this invention are designed to allow the formulation of peptide-containing synthetic lung surfactants with salts containing calcium or other divalent or monovalent ions (as described above) so as to reduce surface or shear viscosity to improve pulmonary delivery as well as maximize shelf life.

The synthetic peptides of the present invention can be synthesized by standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including the Applied Biosystems 431A, 433A synthesizers and Peptide Technologies Symphony or large scale Sonata or CEM Liberty automated solid phase peptide synthesizers. Using the same synthesis strategies, mimics of the surfactant peptides may also be prepared using either oligo-N-substituted glycines to make surface active surfactant peptoids (Seurynck et al., *Chem. Biology* 12:77-88 (2005), which is hereby incorporated by reference in its entirety) or by altering amino acid sequence of the surfactant peptide mimetic by introducing non-proteinaceous amino acids that improve resistance to protease cleavage (e.g., α,α-disubstituted aminoacids, and β-homo amino acids) (Yamaguchi et al., "Effect of alpha, alpha-disubstituted Amino Acids on the Protease Resistance of Peptides," *Biosci., Biotechnol. Biochem.* 67:2269-2272 (2003); Schreiber et al., "On the Biodegradation of beta-Peptides," *Chem. Biol. Chem.* 3:4243-432 (2002), each of which is hereby incorporated by reference in its entirety).

Alternatively, the synthetic peptides can be synthesized in the presence of one or both of the synthetic lipid analogs described above. This aspect of the present invention is described in greater detail below.

The surface-active peptides may be also prepared by using recombinant expression systems. Generally, this involves inserting the nucleic acid molecule into an expression system to which the molecule is heterologous (i.e., not normally present).

One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The nucleic acid molecules can be derived from the known SP-A, SP-B, and SP-C nucleotides using the above-referenced Genbank Accessions. In certain embodiments, it may be desirable to prepare codon-enhanced nucleic acids that will favor expression of the desired peptide in the transgenic expression system of choice.

The preparation of the nucleic acid constructs can be carried out using methods well known in the art. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture. Other vectors are also suitable.

Once a suitable expression vector is selected, the desired nucleic acid sequences are cloned into the vector using standard cloning procedures in the art, as described by Sambrook et al., Molecular Cloning: *A Laboratory Manual, Cold Springs Laboratory*, Cold Springs Harbor, N.Y. (1989), or U.S. Pat. No. 4,237,224 to Cohen and Boyer, which are hereby incorporated by reference in their entirety. The vector is then introduced to a suitable host.

A variety of host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used to carry out this and other aspects of the present invention.

Different genetic signals and processing events control many levels of gene expression (e.g., DNA transcription and messenger RNA ("mRNA") translation). Transcription of DNA is dependent upon the presence of a promoter, which is a DNA sequence that directs the binding of RNA polymerase, and thereby promotes mRNA synthesis. The DNA sequences of eukaryotic promoters differ from those of prokaryotic promoters. Furthermore, eukaryotic promoters and accompanying genetic signals may not be recognized in, or may not function in, a prokaryotic system; similarly, prokaryotic promoters are not recognized and do not function in eukaryotic cells.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters to obtain a high level of transcription and, hence, expression of the gene. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV 5, ompF, bla, lpp, and the like, may be used to direct high levels of transcription of adjacent DNA segments. Additionally, a hybrid trp-lacUV 5 (tac) promoter or other *E. coli* promoters produced by recombinant DNA or other synthetic DNA techniques may be used to provide for transcription of the inserted gene.

Bacterial host strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

When multiple nucleic acid molecules are inserted, the multiple nucleic acid molecules may all be placed under a single 5' regulatory region and a single 3' regulatory region, where the regulatory regions are of sufficient strength to transcribe and/or express the nucleic acid molecules as desired.

Specific initiation signals are also required for efficient gene transcription and translation in prokaryotic cells. These transcription and translation initiation signals may vary in "strength" as measured by the quantity of gene specific messenger RNA and protein synthesized, respectively. The nucleic acid expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used. Depending on the vector system and host utilized, any number of suitable transcription and/or translation elements, including constitutive, inducible, and repressible promoters, as well as minimal 5' promoter elements, enhancers or leader sequences may be used.

Typically, when a recombinant host is produced, an antibiotic or other compound useful for selective growth of only the transgenic cells is added as a supplement to the media. The compound to be used will be dictated by the selectable marker element present in the plasmid with which the host was transformed. Suitable genes are those which confer resistance to gentamycin, G418, hygromycin, streptomycin, spectinomycin, tetracycline, chloramphenicol, and the like. Similarly, "reporter genes," which encode enzymes providing for production of an identifiable compound, or other markers which indicate relevant information regarding the outcome of gene delivery, are also suitable. For example, various luminescent or phosphorescent reporter genes are also appropriate, such that the presence of the heterologous gene may be ascertained visually.

An example of a marker suitable for the present invention is the green fluorescent protein (GFP) gene. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (Prasher et al., "Primary Structure of the *Aequorea Victoria* Green-Fluorescent Protein," *Gene* 111(2):229-233 (1992); U.S. Pat. No. 5,491,084 to Chalfie et al., which are hereby incorporated by reference in their entirety). A plasmid encoding the GFP of *Aequorea victoria* is available from the ATCC as Accession No. 75547. Mutated forms of GFP that emit more strongly than the native protein are commercially available from Clontech Laboratories, Inc. (Palo Alto, Calif.) and can be used for the same purpose. Indeed, any nucleic acid molecule encoding a fluorescent form of GFP can be used in accordance with the subject invention. Standard techniques are then used to place the nucleic acid molecule encoding GFP under the control of the chosen cell specific promoter.

A nucleic acid molecule encoding a suitable cytokine, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Sambrook et al., *Molecular Cloning: A Laboratory Manual*, Cold Spring Laboratory, Cold Spring Harbor, N.Y. (1989); Ausubel et al., "Short Protocols in Molecular Biology," New York:Wiley (1999), and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, yeast, and mammalian cells.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Alternatively, if the peptide of interest of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above.

Whether the peptide of interest is secreted or not, it may also contain a purification tag (such as poly-histidine ($His_6$-), a glutathione-S-transferase (GST-), or maltose-binding protein (MBP-)), which assists in the purification but can later be removed, i.e., cleaved from the peptide following recovery. Protease-specific cleavage sites can be introduced between the purification tag and the desired peptide. The desired peptide product can be purified further to remove the cleaved purification tags.

The surfactant compositions of the present invention can further include any one or more of a non-phospho surfactant or a therapeutic agent including a pharmacological agent.

As used herein, the term "non-phospho surfactant" refers to surface active compounds that do not possess a phospho group (e.g., phosphate, phosphonate, etc.). Exemplary non-phospho surfactants include, without limitation, a free fatty acid, hexadecanol, or cholesterol.

Preferred free fatty acids include saturated and monounsaturated C10 to C24 hydrocarbons, more preferably C12-C20 hydrocarbons, most preferably C14-C18 hydrocarbons. Of these, saturated hydrocarbons are preferred.

The therapeutic agent can be any compound, nucleic acid, or peptide that is intended to be administered to the targeted lung tissues for therapeutic treatment of a disease or disorder involving the affected tissue. Exemplary therapeutic agents include, without limitation, antioxidant enzymes, other antioxidant substances, anti-inflammatory agents (drugs, antibodies, receptor antagonists, and soluble receptors, etc.), vasoactive agents or agents synergistic with vasoactive agents, agents affecting leukocyte function or recruitment, agents affecting platelet aggregation, agents affecting resident pulmonary cells involved in host-defense, and agents participating in gene therapy.

According to one embodiment, the surfactant composition includes the phospholipase-resistant phospho-glycerol derivative and the phospholipase-resistant phospho-choline derivative. Typically, the phospholipase-resistant phospho-glycerol derivative and the phospholipase-resistant phospho-choline derivative are present at a mole ratio or weight ratio of between about 1:1 to about 1:100, preferably about 1:4 to about 1:50, more preferably about 1:6 to about 1:25.

According to another embodiment, the surfactant composition includes the phospholipase-resistant phospho-choline derivative and a surface active peptide, but not the phospholipase-resistant phospho-glycerol derivative. Preferably, the phospholipase-resistant phospho-choline derivative is present in an amount of about 50 to about 99 wt percent, more preferably between about 85 and about 99 wt percent; and the surface active peptide is present in an amount of about 1 to about 15 wt percent, more preferably about 1 to about 5 wt percent.

According to another embodiment, the surfactant composition includes the phospholipase-resistant phospho-choline derivative, the phospholipase-resistant phospho-glycerol derivative, and a surface active peptide. Preferably, the phospholipase-resistant phospho-choline derivative is present in an amount of about 65 to about 95 wt percent, more preferably between about 80 and about 95 wt percent; the phospholipase-resistant phospho-glycerol derivative is present in an amount of about 1 to about 20 wt percent, more preferably between about 1 and about 10 wt percent; and the surface active peptide is present in an amount of about 1 to about 10 wt percent, more preferably about 1 to about 5 wt percent.

Exemplary surfactant compositions are set forth below.

Composition A:

| weight percent | component |
|---|---|
| about 65 to about 99 | phospholipase-resistant phospho-choline derivative |
| about 1 to about 20 | phospholipase-resistant phospho-glycerol derivative |
| up to about 15 | non-phospho surfactant |
| up to about 5 | surface active synthetic peptide. |

Composition B:

| weight percent | component |
|---|---|
| about 80 to about 99 | phospholipase-resistant phospho-choline derivative |
| about 1 to about 10 | phospholipase-resistant phospho-glycerol derivative |
| up to about 10 | non-phospho surfactant |
| about 1 to about 3 | surface active synthetic peptide. |

Composition C:

| weight percent | component |
|---|---|
| about 85 to about 96 | phospholipase-resistant phospho-choline derivative |
| about 2.5 to about 8 | phospholipase-resistant phospho-glycerol derivative |
| up to about 10 | non-phospho surfactant |
| about 1 to about 5 | surface active synthetic peptide |

The surfactant compositions of the present invention can be used to treat lung tissue that is characterized by deficiency and/or dysfunction of endogenous surfactant (i.e., "surfactant deficient or dysfunctional lung tissue"). In certain embodiments, the deficiency of endogenous surfactant can be a reduced amount or an abnormal composition of endogenous surfactant (i.e., not enough is present or the composition thereof is ineffective) or the complete absence of an endogenous surfactant, and the surfactant dysfunction can be a reduced activity of endogenous surfactant either present intrinsically or acquired during disease. Thus, the term "treatment" of surfactant deficient and/or dysfunctional lung tissue is meant to include a prophylactic or therapeutic regimen that can inhibit onset of RDS, for example, in premature infants, or the onset of acute lung injury (ALI) or the acute respiratory distress syndrome (ARDS) in patients of any age, or otherwise improve respiratory function, lung pressure-volume mechanics, or clinical outcome when administered for therapeutic treatment of a pre-existing conditions such as acute or neonatal RDS, or ALI, or ARDS. As used herein, "treatment" contemplates complete therapeutic resolution of a condition as well as improving conditions to minimize symptoms of RDS or ALI/ARDS.

The treatments in accordance with this aspect of the invention involve administering a surfactant composition of the present invention to a patient having lung tissue characterized by endogenous surfactant deficiency and/or dysfunction, where the administering is carried out under conditions effective to coat alveolar surfaces of the affected lung tissue with the surfactant composition, thereby treating the surfactant deficient and/or dysfunctional lung tissue.

The patient to be treated can be a premature infant who is characterized by either the complete absence of endogenous surfactant or an ineffective amount of endogenous surfactant or an acquired dysfunction of endogenous surfactant during the clinical course. In either case, the surfactant composition of the present invention can be administered in a manner effective to prevent onset of neonatal respiratory distress syndrome (when administered immediately following intubation), or reduce the severity of respiratory deficit in acute respiratory distress syndrome and/or acute lung injury (when administered some time after initial intubation). Administration of the surfactant composition is preferably via aspiration, airway instillation, aerosolization, or nebulization. Administration of the surfactant can be administered periodically over a course of treatment to maintain lung function in the infant, preferably until the infant's lung tissue is capable of producing sufficient endogenous surfactant to maintain lung function in the absence of intervention.

The patient to be treated can also be an individual that otherwise should be able to produce active endogenous surfactant, but due to lung tissue disease or disorder either has deficient levels of endogenous surfactant or existing endogenous surfactant has become inhibited or inactivated in activity. In this embodiment, the patient is a full-term infant, child, or adult. Endogenous surfactant production can be deficient due to acute lung injury caused by pulmonary disease or infection, systemic disease or infection, or other direct or indirect causes such as burns, trauma, shock, aspiration syndromes, drug overdose, multiple blood transfusions, pancreatitis, or other known causes of ALI/ARDS. In either acquired surfactant deficiency or dysfunction, the surfactant composition of the present invention can be administered in a manner effective to reduce the severity of respiratory deficit in acute respiratory distress syndrome and/or acute lung injury. The surfactant composition may also be administered prophylactically to such patients to prevent the onset of ALI/ARDS. Administration of the surfactant composition is preferably via aspiration, airway instillation, aerosolization, or nebulization. Administration of the surfactant can be administered periodically over a course of treatment to maintain lung function in the individual being treated.

Prior attempts to synthesize full-length SP-A or SP-B proteins using standard peptide synthesis conditions have resulted in proteins that possess deficient activity, likely due to improper folding during synthesis. It is believed that synthesis of the surface active peptides or full length SP can be enhanced by synthesizing the peptides or proteins in the presence of one or both of the lipid analogs described herein (or any surfactant composition of the present invention). As a consequence, it is believed that the resulting surface-active peptide or SP will have increased surface activity relative to a peptide or protein synthesized in the absence of the compounds or compositions of the present invention. As used here, the term "increased surface activity" is meant to include improved adsorption or dynamic lowering of surface tension. That is, a composition prepared in the presence of a peptide or protein synthesized in this manner will be characterized by lower surface tension when compared to a similar composition where the peptide or protein was prepared using standard peptide coupling procedures in the absence of a lipid analog or composition of the present invention.

Another aspect of the present invention relates to a method of delivering a therapeutic agent. By virtue of the surface activity of the compositions of the present invention, it is believed that the surfactant compositions of the present invention will readily form liposomal vesicles that can be used to deliver therapeutic agents to a patient. Thus, this method of the present invention includes introducing a therapeutic agent into a surfactant composition of the present invention under conditions effective to encapsulate the therapeutic agent in liposomal vesicles, and then administering the composition to a subject under conditions effective to deliver the therapeutic agent to a target tissue. The administration can be any suitable approach for delivery of the therapeutic agent to a target tissue, but preferably aspiration, airway instillation, aerosolization, nebulization, intranasal instillation, oral or nasogastric instillation, intraperitoneal injection, or intravascular injection. The target tissue can be lung tissue or a systemic tissue. The agent or agents to be delivered can be any pharmaceutical or therapeutic agent including those listed above as well as a systemic or local anti-tumor agent, a systemic or local gene therapy agent, a systemic or local anti-inflammatory agent or antioxidant, a systemic or local vasoactive agent, a systemic or local agent modifying immune responses, blood cells, or host-defense.

EXAMPLES

The following examples are intended to illustrate the present invention, but are not intended to limit the scope of the appended claims.

Example 1

Synthesis of Phosphatidylglycerol Lipid Analogs and Intermediates 1,2-dihexadecyl-3 phosphoglycerol 1,2-Dihexadecyl-3 phosphoglycerol was synthesized according to the following protocol. Freshly distilled phosphorus oxychloride (boiling range 105-107° C.) (410 mg, 2.64 mmol) was cooled in an ice-bath. A solution of 1,2-dihexadecylglycerol (1.19 g, 2.20 mmol) and $Et_3N$ (334 mg, 3.3 mmol) in 15 mL of THF was added in dropwise to the phosphorus oxychloride with continuous stirring and the mixture was then stirred at r.t. for 2 h. Solketol (349 mg, 2.64 mmol) in 10 mL of THF and $Et_3N$ (668 mg, 6.6 mmol) was added dropwise. The temperature of the reaction mixture was raised and after 2 h the reaction mixture was filtered by suction to remove the precipitated triethylamine hydrochloride. 1 M $Na_2CO_3$ (aq) was added to the filtrate and stirring continued for 15 h at r.t. Acetone (30 mL) was added to the upper THF phase and the precipitate was removed by filtration. The filtrate was evaporated to dryness. The residue was dissolved in 25 mL of acetic acid (70% in water) and stirred for 2 h. The lipid was extracted with $CHCl_3$ and purified by flash chromatography on silica gel, eluent ($CHCl_3$: MeOH=10:1) to get 730 mg, 48% yield.

Characterization data for rac-1,2-dihexadecyl-3-phosphoglycerol: mp 157-159° C.; IR (neat, $v_{max}$): 3396, 2917, 2850, 1467, 1384, 1226, 1116, 1060 $cm^{-1}$; $^1H$ NMR ($CDCl_3$: $CD_3OD$=4:1, 400 MHz): 3.92 (m, 4H), 3.80 (m, 1H), 3.54-3.62 (m, 6H), 3.35-3.50 (m, 3H), 1.56 (m, 4H), 1.26-1.36 (m, 52H), 0.88 (t, J=6.8 Hz, 6H) ppm; $^{13}C$ NMR ($CDCl_3$:$CD_3OD$=4:1, 100 MHz): 77.4, 71.6, 70.7, 70.4, 70.2, 66.3, 64.7, 62.2, 31.7, 29.7, 29.5, 29.3, 29.1, 25.8 (d, J=6.1 Hz), 22.4, 13.8 ppm; $^{31}P$ NMR ($CDCl_3$:$CD_3OD$=4:1, 162 MHz): 5.8 ppm; HRMS, ESI TOF (-ve), m/z: calc'd for $C_{38}H_{78}O_8P$ [M−H]$^-$: 693.5434; found: 693.5395.

1-hexadecyl-2-hexadec-9-encyl-3 phosphoglycerol

1-Hexadecyl-2-hexadec-9-encyl-3 phosphoglycerol was synthesized according to the following protocol. Freshly distilled phosphorus oxychloride (boiling range 105-107° C.) (292 mg, 1.91 mmol) was cooled in an ice-bath. A solution of 1-hexadecyl-2-hexadec-9-encyl glycerol (823 mg, 1.53 mmol) and $Et_3N$ (232 mg, 2.3 mmol) in 15 mL of THF was added dropwise to the phosphorus oxychloride with continuous stirring and the mixture was then stirred at r.t. for 2 h. Solketol (252 mg, 1.91 mmol) in 10 mL of THF and $Et_3N$ (464 mg, 4.59 mmol) was added dropwise. The temperature of the reaction mixture was raised and after 2 h the reaction mixture was filtered by suction to remove the precipitated triethylamine hydrochloride. 1 M $Na_2CO_3$ (aq) was added to the filtrate and stirring continued for 15 h at r.t. Acetone (30 mL) was added to the upper THF phase and the precipitate was removed by filtration. The filtrate was evaporated to dryness. The residue was dissolved in 20 mL of acetic acid (70% in water) and stirred for 2 h. The lipid was extracted with $CHCl_3$ and purified by flash chromatography on silica gel, eluent ($CHCl_3$:MeOH=10:1) to get 455 mg, 43% yield.

Characterization data for rac-1-hexadecyl-2-hexadec-9-encyl-3-phosphoglycerol: IR (neat, $v_{max}$): $cm^{-1}$:3420, 3195, 3010, 2921, 2851, 1467, 1256, 1240, 1132, 1101, 1058 $cm^{-1}$; $^1H$ NMR ($CDCl_3$:$CD_3OD$=4:1, 400 MHz): 5.30 (m, 2H), 3.90-3.84 (m, 4H), 3.74 (pent, J=4.9 Hz, 1H), 3.63-3.49 (m, 6H), 3.45-3.38 (m, 3H), 1.98 (m, 4H), 1.51 (m, 4H), 1.23 (s, 44H), 0.84 (m, 6H), ppm; $^{13}C$ NMR ($CDCl_3$:$CD_3OD$=4:1, 100 MHz): 129.6, 129.4, 77.6 (d, J=8.2 Hz), 71.4, 70.9 (d, J=5.1 Hz), 70.3, 70.2, 66.1 (d, J=5.7 Hz), 64.7, 62.2, 57.2, 31.6, 31.4, 29.7, 29.4, 29.3, 29.2, 29.0, 28.9, 28.6, 26.8, 25.7 (d, J=3.2 Hz), 22.3 (d, J=3.1 Hz), 13.2 ppm; $^{31}P$ NMR ($CDCl_3$:$CD_3OD$=4:1, 162 MHz): 5.3 ppm; HRMS, ESI TOF (+ve), m/z: calc'd for $C_{38}H_{78}O_8P$ [M+H]$^+$:693.5434; found: 693.5430.

2,3-bis(hexadecyloxy)propyl hydrogen 3,4-dihydroxybtaylphosphonate 2,3-Bis(hexadecyloxy)propyl hydrogen 3,4-dihydroxybutylphosphonate was synthesized by preparing the intermediate lithium dimethylmethanephosphonate (S, Scheme 2). Lithium dimethylmethanephosphonate was prepared by adding a solution of n-butyllithium (2.5M solution in hexane 22.5 mL, 56.2 mmol) to a solution of dimethyl methanephosphonate (6.97 g, 56.2 mmol) in dry THF (60 mL) at −78° C. $BF_3$ $Et_2O$ (7.98 g, 56.2 mmol) was added followed by a solution of R (5.0 g, 28.1 mmol) in dry THF (40 mL). The mixture was stirred at −78° C. for 2.5 h then warm up to r.t. for 2 h. It was then quenched with saturated $NH_4Cl$, extracted with $CH_2Cl_2$, washed with $H_2O$, brine, dried over $MgSO_4$, evaporated, purified by flash chromatography eluent with $CHCl_3$:MeOH=25:1 to get the product 6.4 g, 75% yield.

Characterization data: $^1H$ NMR ($CDCl_3$, 400 MHz): 8.05 (m, 2H), 7.54 (m, 1H), 7.42 (m, 2H), 4.30 (m, 2H), 4.01 (m, 2H), 3.74 (s, 3H), 3.72 (s, 3H), 2.10-1.92 (m, 4H) ppm; $^{13}C$ NMR ($CDCl_3$, 100 MHz): 166.5, 133.0, 129.7, 129.5, 128.3, 68.9 (d, J=14 Hz), 68.3, 52.3 (d, J=6.5 Hz, 26.3 (d, J=4.5 Hz, 20.5 (d, J=140.4 Hz ppm; $^{31}P$ NMR ($CDCl_3$, 162 MHz): 35.6 ppm; IR (neat, $v_{max}$): 3396, 2952, 1717, 1276 $cm^{-1}$.

Compound S (4.4 g, 14.56 mmol) was then dissolved in $CH_2Cl_2$ (60 mL), and $Et_3N$ (1.62 g, 16.02 mmol) and DMAP (178 mg, 1.46 mmol) were added. The mixture was stirred at −10° C. and benzoyl chloride (2.25 g, 16.02 mmol) was added. The mixture was stirred at r.t. overnight and dilute HCl was added. The mixture was extracted with $CH_2Cl_2$, washed with water, brine and dried over $MgSO_4$ After concentration the residue was purified by flash chromatography (eluent with EA:hexane=1:1 then CHCl$_3$:MeOH=20:1) to obtain dimethyl 3,4-bis(benzoyloxy)butyl-1-phosphonate (T), 5.43 g, 92% yield.

Characterization data: $^1$H NMR (CDCl$_3$, 400 MHz): 8.02 (m, 4H), 7.58-7.52 (m, 2H), 7.42 (m, 4H), 5.53 (m, 1H), 4.60 (dd, J=4, 12 Hz, 1H), 4.49 (dd, J=6, 12 Hz, 1H), 3.75 (d, J=5.2 Hz, 3H), 3.73 (d, J=5.2 Hz, 3H), 2.17 (m, 2H), 1.94 (m 2H) ppm; $^{13}$C NMR (CDCl$_3$, 100 MHz): 165.8, 165.6, 133.1, 132.9, 129.5, 129.4, 128.2, 128.1, 71.5 (d, J=17.6 Hz), 64.8, 52.3, 24.0 (d, J=4.1 Hz), 20.5 (d, J=142.8 Hz) ppm; $^{31}$P NMR (CDCl$_3$, 162 MHz): 33.6 ppm; IR (neat, v$_{max}$): 3063, 2953, 1723, 1715, 1280, 1262 cm$^{-1}$.

2,3-Bis(hexadecyloxy)propyl hydrogen 3,4-bis(benzoyloxy)butylphosphonate (V) was prepared by adding neat TMSBr (0.39 mL, 3.06 mmol) dropwise to a solution of compound T (546 mg, 1.39 mmol) dissolved in CH$_2$Cl$_2$ (4 mL) stirring at −30° C. After stirring at −30° C. for 40 min., the mixture was stirred at r.t. for 3 h. After removal of the solvent under anhydrous conditions, a thick oil (U) was obtained. To this oil at r.t. was added CH$_2$Cl$_2$ (5 mL), DMF (2 drops) and oxalyl chloride (0.36 mL, 4.17 mmol). The solution was stirred at r.t. for 30 min. during which time gas evolution was evident. The solvent under anhydrous conditions and residue was heated to 50° C. under vacuum for 1 h. The resulting oil was diluted with CHCl$_3$ (30 mL) and stirred at 0° C. To this solution was added dropwise slowly a solution of Et$_3$N (0.19 mL, 1.39 mmol) and 1,2-dihexadecylglycerol (376 mg, 0.695 mmol) in CHCl$_3$ (30 mL). The solution was allowed to warm to r.t. and was stirred for 48 h. The reaction was quenched by adding water (0.7 mL) and the mixture was stirred for one hour. The majority of solvent removed under vacuum and to the residue was added 15 mL of the CHCl$_3$:MeOH:H$_2$O=10:10:1 solvent system and 18 mL of Amberlite® ion exchange resin. The mixture was stirred for 1 h, was filtered and the resin washed with the same solvent system. The combined organic solvents were removed under vacuum. The resulting residue was dissolved in CH$_2$Cl$_2$ washed with brine, dried over MgSO$_4$. After filtration and concentration the residue was triturated into hot hexanes (3×). The hexanes were removed under vacuum and the crude lipid was purified by flash chromatography (eluent with MeOH:CHCl$_3$=1:20) to get 399 mg of the doubly benzoyl protected phosphonolipid, 65% yield.

Characterization data: $^1$H NMR (CDCl$_3$, 400 MHz): 7.92 (m, 4H), 7.42 (m, 2H), 7.31 (m, 4H), 4.50-4.47 (m, 1H), 4.35 (m, 1H), 3.97-3.91 (m, 2H), 3.48-3.28 (m, 6H), 2.07 (m, 2H), 1.8 (m, 2H), 1.42 (m, 4H), 1.16 (m, 54H), 0.79 (t, J=6.6 Hz, 6H) ppm; $^{13}$C NMR (CDCl$_3$, 100 MHz): 166.0, 165.9, 133.1, 132.9, 129.7, 129.6, 128.3, 77.5, 72.0, 71.7, 70.6, 70.1, 65.2, 64.2, 60.3, 31.9, 29.9, 29.7, 29.6, 29.5, 29.3, 26.0 (d, J=4.3 Hz), 22.6, 14.1 ppm; $^{31}$P NMR (CDCl$_3$, 162 MHz): 31.4 ppm; IR (neat, v$_{max}$): 3300, 3063, 2917, 2850, 1723, 1265, 1071 cm$^{-1}$.

The final product, 2,3-bis(hexadecyloxy)propyl hydrogen 3,4-dihydroxybutylphosphonate (W), was prepared by first dissolving the phosphonate V (364 mg, 0.40 mmol) in MeOH—CH$_2$Cl$_2$ (1:2, 20 mL). K$_2$CO$_3$ (anhy.)(223 mg, 1.62 mmol) was added and the mixture was stirred at r.t for 18 h. Water (5 mL) was added and the pH was adjusted to 2-3 by using 6N HCl. The mixture was extracted with CH$_2$Cl$_2$:MeOH=2:1 (2×20 mL) and the organic extracts were washed with brine, dried over MgSO$_4$ and filtered through Celite®. After removal of the solvent, the residue was purified by flash chromatography (eluent from MeOH:CHCl$_3$=1:10 to MeOH:CHCl$_3$=1:4) to get 169 mg of phosphonolipid W, 65% yield.

Characterization data for rac-2,3-bis(hexadecyloxy)propyl hydrogen 3,4-dihydroxybutylphosphonate: IR (neat, v$_{max}$): 3392, 2917, 2850, 1457, 1180, 1072 cm$^{-1}$; $^1$H NMR (CDCl$_3$, 400 MHz): 3.90 (m, 2H), 3.75 (m, 1H), 3.63-3.56 (m, 5H), 3.51-3.46 (m, 4H), 1.75-1.69 (m, 4H), 1.57 (m, 4H), 1.29 (m, 52H), 0.89 (t, J=6.6 Hz, 6H) ppm; $^{13}$C NMR (CDCl$_3$, 100 MHz): 77.7 (d, J=6.0 Hz), 71.7 (d, J=9.1 Hz), 71.3, 70.2, 69.9, 65.1, 63.1, 31.4, 29.5, 29.2, 29.1, 29.0, 28.9, 25.6 (d, J=4.4 Hz), 22.2, 13.4 ppm; $^{31}$P NMR (CDCl$_3$, 162 MHz): 29.6 ppm; HRMS, ESI TOF (+ve), m/z: calc'd for C$_{39}$H$_{82}$O$_7$P [M+H]$^+$:693.5798; found: 693.5753.

Example 2

Alternative Synthesis of Phosphonodiol Intermediate

Intermediate diol preparation can also be carried out according to Scheme 3, infra. Diethyl 3,4-isopropylidene-3,4-dihydroxybutyl-1-phosphonate (N, n=2) was prepared beginning with a mixture of iodide M (3.34 g, 13.1 mmol) and triethylphosphite (8.67 g, 52.2 mmol), which was heated for 24 h at 145-150° C. The excess triethylphosphite was removed by vacuum distillation to get the product (N).

Characterization data: $^1$H NMR (CDCl$_3$, 400 MHz): 3.95 (m, 6H), 3.39 (m, 1H), 1.67 (m, 4H), 1.18 (m, 12H) ppm; $^{13}$C NMR (CDCl$_3$, 100 MHz): 108.7, 75.2 (d, J=17.1 Hz), 68.5, 61.3, 26.6, 26.5, 25.2, 21.5 (d, J=141.3 Hz), 16.2 ppm; $^{31}$P NMR (CDCl$_3$, 162 MHz): 31.9 ppm; IR (neat, v$_{max}$): 1370, 1248, 1223 cm$^{-1}$.

Diethyl 3,4-dihydroxybutyl-1-phosphonate (O, n=2) was prepared using the obtained product (N). A solution of N (570 mg, 2.14 mmol) and pTSA (60 mg, 0.32 mmol) in MeOH (20 mL) was stirred overnight at r.t. Sufficient NaHCO$_3$(s) was added to neutralize the solution, and stirring was continued for another 10 min. The mixture was filtered, and the filtrate was concentrated. The residue was dissolved in CHCl$_3$ (50 mL) and filtered through Celite®, concentrated, purified by flash chromatography, eluent with CHCl$_3$:MeOH=15:1 to give 400 mg, 83% yield.

Characterization data: $^1$H NMR (CDCl$_3$, 400 MHz): 4.19 (s, 1H), 4.02 (m, 4H), 3.59 (m, 2H), 3.40 (m, 1H), 1.96-1.84 (m, 1H), 1.66 (m, 3H), 1.25 (m, 6H) ppm; $^{13}$C NMR (CDCl$_3$, 100 MHz): 71.7 (d, J=14.3 Hz), 66.3, 61.7 (d, J=6.0 Hz), 25.8, 21.6 (d, J=140.1 Hz), 16.3 (d, J=5.7 Hz) ppm; $^{31}$P NMR (CDCl$_3$, 162 MHz): 33.6 ppm; IR (neat, v$_{max}$): 3382, 1219 cm$^{-1}$.

Diethyl 3,4-bis(dinitrobenzoyloxy)butyl-1-phosphonate (P, n=2,3,5-dinitrobenzoyl)) was prepared using the obtained product (O). Compound O (980 mg, 4.38 mmol), Et$_3$N (975 mg, 9.64 mmol) and DMAP (53 mg, 0.44 mmol) were dissolved in CH$_2$Cl$_2$ (60 mL) and cooled to −40° C. 3,5-Dinitrobenzoyl chloride (2.22 g, 9.64 mmol) in CH$_2$Cl$_2$ (10 mL) was added to above solution at −40° C. and the mixture was stirred at r.t. for 2.5 h. Then satd. NH$_4$Cl was added to quench the reaction, extracted with CH$_2$Cl$_2$, washed with water and brine, dried over MgSO$_4$, evaporated the solvent to get the residue which was purified by flash chromatography with eluent CH$_2$Cl$_2$:MeOH=5:1 to get the compound P 2.25 g, 85% yield.

Characterization data: $^1$H NMR (CDCl$_3$, 400 MHz): 9.25 (m, 1H), 9.22 (m, 1H), 9.15 (d, J=2.4 Hz, 2H), 9.08 (m, 2H), 5.71 (m, 1H), 4.92 (dd, J=2.8, 12.4 Hz, 1H), 4.57 (dd, J=7.2, 12.4 Hz, 1H), 4.15 (m, 4H), 2.25 (m, 2H), 1.98-1.92 (m, 2H), 1.36 (t, J=7.2 Hz, 3H), 1.35 (t, J=7.2 Hz, 3H) ppm; $^{13}$C NMR (CDCl$_3$, 100 MHz): 162.2, 148.7, 148.6, 132.9, 132.8, 129.5, 129.4, 122.8, 122.7, 73.8 (d, J=15.8 Hz), 66.5, 62.0, 61.9, 24.1, 21.7 (d, J=143.7 Hz), 16.4, 16.3 ppm; $^{31}$P NMR (CDCl$_3$, 162 MHz): 29.7 ppm; IR (CH$_2$Cl$_2$, v$_{max}$): 3096, 3058, 1738, 1538, 1261, 1160, 727 cm$^{-1}$.

This material (P) or the corresponding dimethyl 3,4-bis (3,5-benzoyloxy)butyl-1-phosphonate (T) can be used for subsequent phosphorylation of the various glycerols and phosphonolipid formation in accordance with Example 1 (Scheme 2).

Example 3

Representative Synthesis and Chemical Characterization of Super Mini-B Peptide (SEQ ID NO: 13)

This example is generally applicable to the synthesis of the majority of the peptides in this patent, although it also contains features specific for Super Mini-B peptide (SEQ ID NO: 13). Chemical synthesis of Super Mini-B was done as a stepwise process with initial assembly of linear sequence using an Applied Biosystems ABI 431A solid phase peptide synthesizer configured for FastMoc™ chemistry (Fields et al., "HBTU Activation for Automated Fmoc Solid-phase Peptide Synthesis," *Peptide Res* 4:95-101 (1991), which is hereby incorporated by reference in its entirety). A low substitution (0.3 mmole/g) pre-derivatized Fmoc-serine (tBu) resin was used to minimize the formation of truncated sequences. To achieve appropriate pairing of disulfide residues to maintain key molecular connectivities, Cys residues at positions 8 and 40 in the linear Super Mini-B molecule were coupled by using acid-labile Fmoc-Cys trityl [Fmoc-Cys(Trt)], while acid-resistant Fmoc-Cys acetamidomethyl (ACM) side chain-protecting groups were employed for Cys insertion at positions 11 and 34. In addition, Fmoc Gln (DMCP)-OH, which has greater solubility in coupling solvent (Carpino et al., "Novel Carboxylic Acid and Carboxamide Protective Groups Based on the Exceptional Stabilization of the Cyclopropylmethyl Cation," *J Org Chem* 60:7718-7719 (1995), which is hereby incorporated by reference in its entirety) was used for the Glu residues in the Super Mini-B sequence, as opposed to more conventional Fmoc-Gln(Trt)-OH that has limited solvent solubility and lower coupling efficiency. All residues were double-coupled using standard Fmoc or FastMoc™ coupling times to insure optimal yield.

After synthesis of the linear Super Mini-B sequence, the peptide was cleaved from the resin and deprotected using 0.75 gm phenol, 0.25 ml ethanedithiol, 0.5 ml of thioanisole, 0.5 ml of deionized water and 10 ml trifluoroacetic acid per gram of resin. The cleavage-deprotection mixture was chilled to 5° C., added to the resin while stirring, and allowed to come to 25° C. with continuous stirring over a period of 2 hrs to insure complete deprotection. The crude peptide was separated from the resin by vacuum-assisted filtration in the cleavage-deprotection solution, followed by washing the resin on a medium porosity sintered glass filter, first with trifluoroacetic acid and then with dichloromethane, to remove residual peptide. The filtrate containing the peptide was precipitated with ice-cold tertiary butyl ether and separated from the ether deprotection solution by centrifugation at 2000×g for 10 min. The precipitate was then subjected to several ether-peptide-precipitation centrifugation cycles to remove excess amounts of cleavage-deprotection byproducts. The crude peptide, which was in the reduced state, was then dissolved in trifluoroethanol (TFE): 10 mM HCl (1:1, v:v) and freeze-dried to a uniform powder consistency that could easily be dissolved in organic solvents for further purification. Crude peptide was purified using preparative scale HPLC with a reversed phase Vydac C8 column and the mass of the peptide (Super Mini-B reduced mass=4899.2463 Daltons) was confirmed by MALDI TOF mass spectrometry.

The folding of HPLC-purified, reduced Super Mini-B peptide into a disulfide-linked helix-hairpin was then facilitated by incubation of purified peptide (0.1 mg/ml) for at least 24 hr at 25° C. in a solution of TFE and 10 mM ammonium bicarbonate buffer (4:6, v:v) at pH 8.0 to oxidize the intramolecular disulfide linkage between Cys 9 and Cys 40. TFE is an ideal solvent for peptides like Super Mini-B, because it interacts with the peptide backbone so as to optimize both the helical sequence and the turn of the engineered bend domain. Buffered TFE solvent enhances the specific folding of Super Mini-B to form a helix-hairpin structure with the N- and C-terminal helical domains in close proximity, which is a preferred geometry for optimal disulfide connectivities. The final intramolecular disulfide linkage between Cys 11 and Cys 34 in Super Mini-B was then accomplished by iodine oxidation of the ACM-protected side chains (Albericio et al., "Preparation and Handling of Peptides Containing Methionine and Cysteine," *In: Fmoc Solid Phase Peptide Synthesis*, Cahn and White, editors, Oxford University Press, New York, p. 102 (2000), which is hereby incorporated by reference in its entirety). Following oxidation, Super Mini-B peptide was re-purified by reverse phase HPLC using the same boundary conditions as employed for the crude material.

The molecular mass of the final oxidized peptide (oxidized Super Mini-B mass=4751.0146 Daltons) was confirmed by Maldi TOF mass spectroscopy, and peptide concentration is obtained spectrophotometrically based on its strong UV absorbance at 280 nm and its calculated molar extinction coefficient of 7210 $M^{-1}$ $cm^{-1}$ (Pace et al., "How to Measure and Predict the Molar Absorption Coefficient of a Protein," *Protein Science* 4:2411-2423 (1995), which is hereby incorporated by reference in its entirety) based on the Beer-Lambert law: $A=\epsilon lC$, where A is absorbance, $\epsilon$ is the molar extinction coefficient, l is the sample cuvette pathlength in centimeters, and C is the molar concentration of peptide. The secondary structure oxidized Super Mini-B was confirmed by Fourier transform infrared (FTIR) spectroscopy at 25° C. using a Bruker Vector 22™ FTIR spectrometer (Pike Technologies) with a DTGS detector, averaged over 256 scans at a gain of 4 and a resolution of 2 $cm^{-1}$. Proportions of α-helix, β-turn, β-sheet, and disordered conformations were determined by Fourier self-deconvolution of the peptide amide I bands using band narrowing and area calculations of component peaks of FTIR spectra using curve-fitting software supplied by Galactic Software (GRAMS/32, version 5; Galactic Industries Corp., Salem, N.H.) and the following frequency limits: α-helix (1662-1645 $cm^{-1}$), β-sheet (1637-1613 and 1710-1682 $cm^{-1}$), β-turns (1682-1662 $cm^{-1}$), and disordered or random (1650-1637 $cm^{-1}$) (Byler and Susi, "Examination of the Secondary Structure of Protein by Deconvolved FTIR Spectra," *Biopolymers* 25:469-487 (1986), which is hereby incorporated by reference in its entirety). Super Mini-B in the TFE solvent system had a secondary structure of approximately 45% helix, 12% turn, 20% beta sheet and 23% disordered (random) conformations.

Super Mini-B peptide was also characterized in terms of its binding (association) affinity for lipids by plasmon resonance using a Biacore 3000 system (Biacore, Uppsala, Sweden). Peptide self-films were chemically-linked using a CM5 sensor chip (BR-1000-14, research grade), and lipid liposomes in running buffer were flowed over the chip to determine the degree of specific lipid association with the peptide film at 37° C. The off and on rates and dissociation constant KD ($KD=k_{off}/k_{on}$) were calculated by BIAevaluation Software Version 4.1. Binding isotherms showed that Super Mini-B had a KD values of 0.063 µM for DEPN-8 and 0.769 µM for dipalmitoyl phosphatidylcholine (DPPC), with the lower KD indicating a greater binding affinity for the ether lipid derivative (DEPN-8).

Example 4

Formulation and Testing of Synthetic Lung Surfactants

Surfactant compositions were formulated using various molar or wt ratios of lipid analogs or naturally occurring lipids, with the addition of native lung surface proteins or synthetic peptides, and optionally a saturated free fatty acid in the indicated wt percentage based on the total weight of the intermediate lipid formulation. Surfactant compositions were dispersed in 0.15 M NaCl+2 mM $CaCl_2$ and placed in a sample chamber mounted on the pulsator unit of a bubble surfactometer. All surfactants were studied at a lipid concentration of 2.5 mg/ml, and in addition a mixture of synthetic ester-linked phospholipids (SLM) plus Super Mini-B was studied at a lipid concentration of 1 mg/ml.

As shown in Table 1, surface tension at minimum bubble radius (minimum surface tension) is tabulated as a function of time of pulsation on a bubble surfactometer (General Transco, Largo, Fla.) (37° C., 20 cycles/min, 50% area compression). A tiny air bubble was formed and pulsated between maximum and minimum radii of 0.55 and 0.4 mm, respectively, while the pressure drop across the air-water interface of the bubble was measured with a precision transducer. Surface tension was calculated from the measured pressure drop at minimum radius (0.4 mm) from the Laplace equation (Enhorning, "Pulsating Bubble Technique for Evaluation of Pulmonary Surfactant," *J Appl Physiol* 43:198-203 (1977); Hall et al., "Approximations in the Measurement of Surface Tension with the Oscillating Bubble Surfactometer," *J Appl Physiol* 75:468-477 (1993), each of which is hereby incorporated by reference in its entirety).

The high surface activity of synthetic lung surfactants containing DEPN-8 or 9:1 DEPN-8:PG-A or 9:1 DEPN-8:PG-B plus 1.5% by weight of Mini-B, FK20, or $F_4K$ is shown in Table 1. Activity is also shown for mixtures containing two glycerophospholipids found in endogenous lung surfactant, 8:2 (molar ratio) dipalmitoyl phosphatidylcholine (DPPC) and palmitoyl-oleoyl phosphatidylglycerol (POPG), with or without added synthetic peptides. Also studied is a synthetic lipid mixture containing 16:10:6:1:2 (by weight) DPPC, palmitoyl-oleoyl-phosphatidylcholine (POPC), POPG, palmitoyl-oleoyl-phosphatidylethanolamine (POPE), and cholesterol combined with Super Mini B (SEQ ID NO: 13). The surface activity of DEPN-8+1.5% bovine SP-B/C (mixture of bovine surfactant proteins B/C purified on a column from extracted calf lung surfactant) is additionally shown as a positive control. As described in the preceding paragraph, the surface activity measurements in Table 1 were obtained with a pulsating bubble surfactometer in vitro. Measurements of surface activity on this instrument reflect the combined effects of adsorption and dynamic film compression at a cycling rate (20 cycles/min), temperature (37° C.), and area compression (50% compression from maximum to minimum area) relevant for the mammalian lungs in vivo (Notter, *Lung Surfactants: Basic Science and Clinical Applications*, Marcel Dekker, Inc, New York (2000); Enhorning, "Pulsating Bubble Technique for Evaluation of Pulmonary Surfactant," *J Appl Physiol* 43:198-203 (1977); Notter et al., "Pulmonary Surfactant: Physical Chemistry, Physiology and Replacement," *Rev Chem Eng* 13:1-118 (1997), each of which is hereby incorporated by reference in its entirety). Prior publications have shown that assessments of surface activity on the bubble apparatus correlate well with the physiological activity of exogenous surfactants in animal lungs (see Notter, *Lung Surfactants: Basic Science and Clinical Applications*, Marcel Dekker, Inc, New York (2000); Notter et al., "Pulmonary Surfactant: Physical Chemistry, Physiology and Replacement," *Rev Chem Eng* 13:1-118 (1997); Holm et al., "Effects of Hemoglobin and Cell Membrane Lipids on Pulmonary Surfactant Activity," *J Appl Physiol* 63:1434-1442 (1987), each of which is hereby incorporated by reference in its entirety). As shown in Table 1, addition of 1.5% by weight of Super Mini-B, Mini-B, FK20, or $F_4K$ to DEPN-8 or 9:1 DEPN-8:PG-A or 9:1 DEPN-8:PG-B resulted in superior surface activity (lower minimum surface tensions during bubble pulsation) compared to DEPN-8 alone, 8:2 DPPC:POPG alone (negative control), or surfactant mixtures containing 8:2 DPPC:POPG plus peptides. The activity of these surfactant formulations of the present invention also approached or exceeded the positive control DEPN-8+1.5% bovine SP-B/C. Surfactant mixtures containing 9:1 DEPN-8:PG-A or 9:1 DEPN-8:PG-B combined with 1.5% bovine SP-B/C also had greater surface activity than the positive control DEPN-8+1.5% bovine SP-B/C (Table 1). These data indicate that the combination of phospholipase-resistant phospho-choline derivatives and phospholipase-resistant phospho-glycerol derivatives improves surfactant function, and that activity is further enhanced by the inclusion of specific synthetic peptides. In addition, bubble surfactometer results for Super Mini-B showed that this exemplary peptide not only had very high surface activity when combined with synthetic lipid analogs (DEPN-8 or 9:1 DEPN-8:PG-B), but also had high surface activity when combined with SLM containing ester-linked glycerophospholipids plus cholesterol (Table 1). This latter result documents that the Super Mini-B peptide can be used as a highly-active ingredient in synthetic exogenous lung surfactants containing ester-linked phospholipids, in addition to being used in synthetic lung surfactants that contain phospholipase-resistant lipid analogs such as DEPN-8 or DEPN-8 plus a PG analog.

TABLE 1

Surface Activity of Synthetic Surfactants Containing Lipid Analogs Plus Peptides and Biological Lipids Plus Peptides

| Surfactant Mixture | Surface tension (mN/m) at minimum bubble radius at time (min) | | | | | | | |
|---|---|---|---|---|---|---|---|---|
| | 0.25 | 0.5 | 1 | 2 | 5 | 10 | 15 | 20 |
| 9:1 DEPN-8:PG-A + 1.5% Mini-B | 13 ± 2 | 9 ± 0 | 4 ± 1 | <1 | | | | |
| 9:1 DEPN-8:PG-B + 1.5% Mini-B | 12 ± 0 | 10 ± 1 | 3 ± 1 | <1 | | | | |
| 9:1 DEPN-8:PG-A + 1.5% Mini-B + 5% PA | 10 ± 1 | 9 ± 1 | 2 ± 2 | <1 | | | | |
| DEPN-8 + 1.5% FK20 | 18 ± 1 | 13 ± 1 | 7 ± 1 | 3 ± 1 | <1 | | | |
| DEPN-8 + 1.5% $F_4K$ | 17 ± 1 | 14 ± 1 | 11 ± 1 | 3 ± 1 | <1 | | | |
| DEPN-8 | 32 ± 2 | 27 ± 2 | 21 ± 2 | 14 ± 2 | 6 ± 1 | 2 ± 1 | <1 | |

TABLE 1-continued

Surface Activity of Synthetic Surfactants Containing Lipid Analogs Plus Peptides and Biological Lipids Plus Peptides

| Surfactant Mixture | Surface tension (mN/m) at minimum bubble radius at time (min) | | | | | | | |
|---|---|---|---|---|---|---|---|---|
| | 0.25 | 0.5 | 1 | 2 | 5 | 10 | 15 | 20 |
| DEPN-8 + 1.5% SP-B/C bovine | 13 ± 1 | 7 ± 1 | 4 ± 1 | 3 ± 0 | <1 (3 min) | | | |
| 9:1 DEPN-8:PG-A + 1.5% SP-B/C bovine | 10 ± 1 | 3 ± 1 | 2 ± 1 | <1 | | | | |
| 9:1 DEPN-8:PG-B + 1.5% SP-B/C bovine | 8 ± 0 | 3 ± 0 | 2 ± 0 | <1 | | | | |
| DEPN-8 + 1.5% Super Mini-B | 8 ± 1 | 2 ± 1 | <1 | | | | | |
| 9:1 DEPN-8:PG-B + 1.5% Super Mini-B | 6 ± 1 | 1 ± 1 | <1 | | | | | |
| 8:2 DPPC:POPG | 43 ± 7 | 34 ± 3 | 27 ± 4 | 23 ± 2 | 20 ± 1 | 19 ± 1 | 18 ± 1 | 17 ± 0 |
| 8:2 DPPC:POPG + 1.5% Mini-B | 21 ± 1 | 21 ± 1 | 18 ± 0 | 18 ± 0 | 16 ± 0 | 14 ± 0 | 13 ± 0 | 12 ± 0 |
| 8:2 DPPC:POPG + 1.5% FK20 | 22 ± 2 | 20 ± 2 | 19 ± 2 | 16 ± 2 | 11 ± 1 | 7 ± 0 | 6 ± 0 | 6 ± 0 |
| 8:2 DPPC:POPG + 1.5% $F_4K$ | 20 ± 2 | 19 ± 1 | 16 ± 1 | 14 ± 1 | 12 ± 1 | 8 ± 1 | 5 ± 1 | <1 |
| SLM (1.0 mg/ml) + 1.43% Super Mini-B | 27 ± 1 | 23 ± 1 | 20 ± 1 | 14 ± 1 | 7 ± 1 | 1 ± 1 | <1 | |
| SLM (2.5 mg/ml) + 1.43% Super Mini-B | 10 ± 2 | 4 ± 1 | <1 | | | | | |

Data are Mean ± SEM for n = 3-6. All total lipid concentrations for bubble experiments were 2.5 mg/ml except for SLM (1.0 mg/ml); peptide contents are given in weight percent relative to lipid.
Abbreviations:
DPPC, dipalmitoyl phosphatidylcholine;
POPG, palmitoyl-oleoyl phosphatidylglycerol;
8:2 (by mole) DPPC:POPG (negative control);
SLM: synthetic lipid mixture containing 16:10:6:1:2 (by weight) DPPC:POPC (palmitoyl oleoyl-PC):POPG:POPE (palmitoyl-oleoyl-phosphatidylethanolamine):cholesterol;
SP-B/C bovine, mixture of surfactant proteins B/C purified from calf lung surfactant extract (positive control for peptides);
PA, palmitic acid (5% by weight);
DEPN-8: phospho-choline analog defined in the text [0058];
PG-A, PG-B, and PG-C are phospho-glycerol phospho(no)lipids defined in the text [0047];
Super Mini-B, SEQ ID NO: 13;
Mini-B, SEQ ID NO: 4;
FK20, SEQ ID NO: 26; and
$F_4K$, SEQ ID NO: 27.

Example 5

Resistance of Synthetic Surfactants Containing DEPN-8 and Peptides to Degradation by Phospholipase $A_2$ ($PLA_2$)

Synthetic surfactants containing DEPN-8 plus synthetic peptides with or without PG phosphonolipids have a resistance to degradation by phospholipases that has potential advantages for treating surfactant dysfunction in clinical lung injuries where these inflammatory enzymes are present.

The surfactant compositions listed in Table 2 were prepared and then incubated in vitro with $PLA_2$ (0.1 Units/ml) for 30 min at 37° C. to assess lipid degradation. Degradation was assessed by measuring lipid classes in weight percent based on phosphate analysis of thin layer chromatographic bands separated by solvent system C of Touchstone et al., "Improved Separation of Phospholipids in Thin-layer Chromatography," Lipids 15:61-62 (1980), which is hereby incorporated by reference in its entirety.

Both synthetic surfactants (DEPN-8+Mini-B (SEQ ID NO: 4) and DEPN-8+FK20 (SEQ ID NO: 26)) maintained full chemical integrity in the presence of $PLA_2$. In contrast, calf lung surfactant extract (CLSE) is significantly degraded by $PLA_2$ as shown by Wang et al. ("Surface Activity of a Synthetic Lung Surfactant Containing a Phospholipase-resistant Phosphonolipid Analog of Dipalmitoyl Phosphatidylcholine," Am J Physiol 285:L550-L559 (2003), which is hereby incorporated by reference in its entirety), with a substantial decrease in its content of phosphatidylcholine and a substantial increase in lysophosphatidylcholine (Table 2). This latter lyso-lipid class of degradation products of phospholipase activity is known to be highly inhibitory to lung surfactant activity (Enhorning et al., "Phospholipases Introduced into the Hypophase Affect the Surfactant Film Outlining a Bubble," J Appl Physiol 73:941-945 (1992); Holm et al., "Multiple Mechanisms of Lung Surfactant Inhibition," Pediatr Res 46:85-93 (1999); Wang et al., "Additivity of Protein and Non-Protein Inhibitors of Lung Surfactant Activity," Am J Respir Crit Care Med 158:28-35 (1998); Wang et al., "Surfactant Activity and Dysfunction in Lung Injury," In Lung Injury: Mechanisms, Pathophysiology, and Therapy, Notter et al. (eds.), Taylor Francis Group, Inc, Boca Raton, pp. 297-352 (2005), each of which is hereby incorporated by reference in its entirety).

TABLE 2

Resistance of Synthetic Lung Surfactants Containing DEPN-8 + Peptides to Chemical Degradation from Phospholipase $A_2$

| Phospholipid (phosphonolipid) Class | CLSE | CLSE + $PLA_2$ | DEPN-8 + 1.5% Mini-B ± $PLA_2$ | DEPN-8 + 1.5% FK20 ± $PLA_2$ |
|---|---|---|---|---|
| Lysophosphatidylcholine | 0.4 ± 0.2 | 29.5 ± 2.4 | | |
| Sphingomyelin | 1.0 ± 0.2 | 1.2 ± 0.5 | | |
| Phosphatidylcholine/phosphocholine | 84.4 ± 0.4 | 55.1 ± 3.2 | 100 ± 0 | 100 ± 0 |
| Phosphatidylinositol | 4.0 ± 0.6 | 3.8 ± 0.7 | | |

TABLE 2-continued

Resistance of Synthetic Lung Surfactants Containing DEPN-8 + Peptides to Chemical Degradation from Phospholipase $A_2$

| Phospholipid (phosphonolipid) Class | CLSE | CLSE + $PLA_2$ | DEPN-8 + 1.5% Mini-B ± $PLA_2$ | DEPN-8 + 1.5% FK20 ± $PLA_2$ |
|---|---|---|---|---|
| Phosphatidylethanolamine | 3.7 ± 0.7 | 3.8 ± 1.0 | | |
| Phosphatidylglycerol | 4.7 ± 0.3 | 4.1 ± 0.6 | | |
| Residue | 1.8 ± 0.2 | 2.5 ± 0.2 | | |

Data are mean ± SEM for n = 3. Results for calf lung surfactant extract (CLSE) are from Wang et al., "Surface Activity of a Synthetic Lung Surfactant Containing a Phospholipase-resistant Phosphonolipid Analog of Dipalmitoyl Phosphatidylcholine," *Am J Physiol* 285: L550-L559 (2003), which is hereby incorporated by reference in its entirety.

Example 6

Resistance of Synthetic Surfactants Containing DEPN-8 and Peptides to Biophysical Inhibition from Serum Albumin In addition to resisting chemical degradation by phospholipases in injured lungs, another beneficial property for synthetic exogenous surfactants for potential use in treating ALI/ARDS is being able to resist biophysical inhibition from plasma proteins that transudate into the pulmonary interstitium and alveolar lumen following permeability damage to the alveolocapillary membrane. Albumin is an important example of such an inhibitor (e.g., Wang et al., "Additivity of Protein and Non-Protein Inhibitors of Lung Surfactant Activity," *Am J Respir Crit Care Med* 158:28-35 (1998); Wang et al., "Surfactant Activity and Dysfunction in Lung Injury," *In Lung Injury: Mechanisms, Pathophysiology, and Therapy*, Notter et al. (eds.), Taylor Francis Group, Inc, Boca Raton, pp. 297-352 (2005); Holm et al., "Surface Property Changes from Interactions of Albumin with Natural Lung Surfactant and Extracted Lung Lipids," *Chem Phys Lipids* 38:287-298 (1985), each of which is hereby incorporated by reference in its entirety). DEPN-8 in mixtures with 1.5% by weight Mini-B (SEQ ID NO: 4), FK20 (SEQ ID NO: 26), or $F_4K$ (SEQ ID NO: 27) had a significant ability to resist biophysical inhibition by bovine serum albumin (Table 3). The ability of mixtures of DEPN-8 (2.5 mg/ml)+1.5% Mini-B, FK20, or $F_4K$ to overcome biophysical inhibition from serum albumin was similar to that of the bovine lung surfactant extract CLSE (2.5 mg/ml) (Table 3). CLSE serves as an activity standard for the most active form of surfactant obtained from animal lungs, and it is known to be superior to several current clinical exogenous lung surfactants in its ability to resist biophysical inhibition by albumin or other blood proteins (see Notter, *Lung Surfactants: Basic Science and Clinical Applications*, Marcel Dekker, Inc, New York (2000); Notter et al., "Pulmonary Surfactant: Physical Chemistry, Physiology and Replacement," *Rev Chem Eng* 13:1-118 (1997), each of which is hereby incorporated by reference in its entirety).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

TABLE 3

Surface Activity of DEPN-8 + 1.5% by weight Synthetic Peptide + Bovine Serum Albumin (BSA)

| Surfactant Mixture (3 mg/ml BSA, 2.5 mg/ml surfactant lipid) | Surface tension (mN/m) at minimum bubble radius at time (min) | | | | | |
|---|---|---|---|---|---|---|
| | 0.25 | 0.5 | 1 | 2 | 5 | 10 |
| DEPN-8 + 1.5% Mini-B | 25 ± 1 | 22 ± 1 | 19 ± 1 | 10 ± 2 | 4 ± 1 | <1 |
| DEPN-8 + 1.5% FK20 | 23 ± 1 | 20 ± 0 | 17 ± 0 | 10 ± 2 | 3 ± 1 | <1 |
| DEPN-8 + 1.5% $F_4K$ | 24 ± 1 | 21 ± 1 | 17 ± 1 | 10 ± 1 | 3 ± 1 | <1 |
| CLSE | 20 ± 1 | 16 ± 1 | 14 ± 2 | 11 ± 2 | 5 ± 2 | <1 |

Data are Mean ± SEM for n = 4-5. Surface tension at minimum radius (minimum surface tension) is shown as a function of time of pulsation on a bubble surfactometer (37° C., 20 cycles/min, 50% area compression, 2.5 mg/ml phosphonolipid concentration for synthetic surfactants and 2.5 mg/ml phospholipid concentration for CLSE).

What is claimed is:

1. A lung surfactant composition comprising:
   a phospholipase-resistant phospho-glycerol compound according to formulae (Ia) or (Ib)

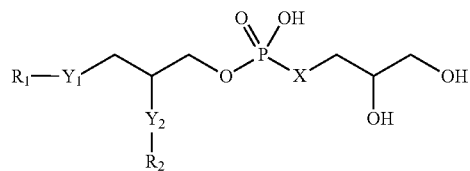

(Ia)

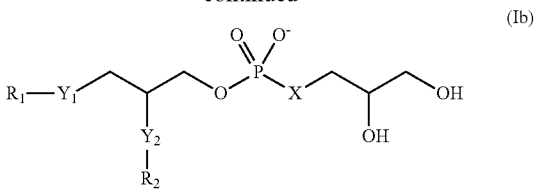

(Ib)

wherein,
X is O or $(CH_2)_n$ where n is an integer from 0 to 5,
$Y_1$ and $Y_2$ are independently O, S, or $SO_2$, and
$R_1$ and $R_2$ are independently C8-C24 hydrocarbons; and
a phospholipase-resistant phospho-choline compound according to formula (II)

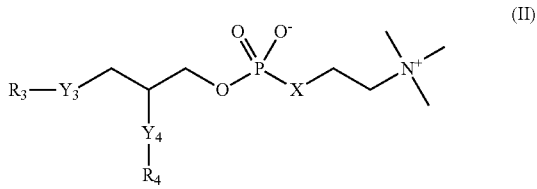

(II)

wherein

X is O or $(CH_2)_n$ where n is an integer from 0 to 5, $Y_3$ and $Y_4$ are independently O, S, or $SO_2$, and $R_3$ and $R_4$ are independently C8-C24 hydrocarbons.

2. The lung surfactant composition according to claim 1, wherein $R_1$ and $R_2$ are the same.

3. The lung surfactant composition according to claim 1, wherein $R_1$ and $R_2$ are different.

4. The lung surfactant composition according to claim 1, wherein $R_1$ and $R_2$ are independently saturated, monounsaturated, or polyunsaturated hydrocarbons.

5. The lung surfactant composition according to claim 1, wherein $R_1$ is saturated and $R_2$ is monounsaturated or polyunsaturated.

6. The lung surfactant composition according to claim 1, wherein $R_1$ and $R_2$ are independently C14-C18 hydrocarbons.

7. The lung surfactant composition according to claim 1, wherein X is O.

8. The lung surfactant composition according to claim 1, wherein X is $(CH_2)_n$.

9. The lung surfactant composition according to claim 8, wherein n is an integer from 0 to 2.

10. The lung surfactant composition according to claim 1, wherein $Y_1$ and $Y_2$ are the same.

11. The lung surfactant composition according to claim 10, wherein $Y_1$ and $Y_2$ are both O.

12. The lung surfactant composition according to claim 1, wherein $Y_1$ and $Y_2$ are different.

13. The lung surfactant composition according to claim 12, wherein $Y_2$ is O and $Y_1$ is S or $SO_2$.

14. The lung surfactant composition according to claim 1, wherein the compound has the structure according to formula (Ib) and is present in the form of a salt.

15. The lung surfactant composition according to claim 1, wherein the phospholipase-resistant phospho-glycerol compound is selected from the group consisting of 2,3-bis(hexadecyloxy)propyl 2,3-dihydroxypropyl hydrogen phosphate; 2-((Z)-hexadec-9-enyloxy)-3-(hexadecyloxy)propyl 2,3-dihydroxypropyl hydrogen phosphate; 2,3-bis(hexadecyloxy)propyl hydrogen 3,4-dihydroxybutylphosphonate; 2-(hexadecyloxy)-3-(hexadecylthio)propyl 2,3-dihydroxypropyl hydrogen phosphate; 2-(hexadecyloxy)-3-(hexadecylsulfonyl)propyl 2,3-dihydroxypropyl hydrogen phosphate; 2-((E)-hexadec-9-enyloxy)-3-(hexadecylthio)propyl 2,3-dihydroxypropyl hydrogen phosphate; 2-(E)-hexadec-9-enyloxy)-3-(hexadecylsulfonyl)propyl 2,3-dihydroxypropyl hydrogen phosphate; 2-(hexadecyloxy)-3-(hexadecylthio) propyl hydrogen 3,4-dihydroxybutylphosphonate; 2-(hexadecyloxy)-3-(hexadecyl sulfonyl)propyl hydrogen 3,4-dihydroxybutylphosphonate; 2-((E)-hexadec-9-enyloxy)-3-(hexadecylthio)propyl hydrogen 3,4dihydroxybutylphosphonate; 2-((E)-hexadec-9-enyloxy)-3-(hexadecyl sulfonyl)propyl hydrogen 3,4-dihydroxybutylphosphonate; and combinations thereof.

16. The lung surfactant composition according to claim 1, wherein the phospholipase-resistant phospho-choline compound is selected from the group consisting of [(+)-trimethyl (3-phosphonopropyl)ammonium, mono(2,3-bis(hexadecyloxy)propyl ester]; [(+)-trimethyl(3-phosphonopropyl) ammonium, mono(2-hexadec-9-enyloxy-3-hexadecyloxypropyl) ester] ("DEPN-8"); [(+)-trimethyl(3-phosphonopropyl)ammonium, mono(2-hexadecyloxy-3-hexadecylsulfanylpropyl) ester]; [(+)-trimethyl(3-phosphonopropyl)ammonium, mono(2-hexadecyloxy-3-hexadecylsulfonylpropyl) ester]; and combinations thereof.

17. The lung surfactant composition according to claim 1, wherein the phospholipase-resistant phospho-glycerol compound and the phospholipase-resistant phospho-choline derivative are present in a ratio of between about 1:1 up to about 1:100.

18. The lung surfactant composition according to claim 1 further comprising a non-phospho surfactant.

19. The lung surfactant composition according to claim 1 further comprising one or more lung surfactant proteins or a surface active synthetic peptide.

20. The lung surfactant composition according to claim 19 wherein the surface active synthetic peptide is selected from the group consisting of

SEQ ID NO: 4
CWLCRALIKRIQAMIPKGGRMLPQLVCRLVLRCS,

SEQ ID NO: 5
CWFCRFFFKRFFFFFPKGGRFFPFFFCRFFFRCS,

SEQ ID NO: 6
CWFCRAFIKRFQAMIPKGGRMLPQLVCRLVLRCS,

SEQ ID NO: 7
CWLCRALIKRIQAMIPKGGRMFPQFFCRFFFRCS,

SEQ ID NO: 8
CWFCRAFIKRFQAMIPKGGRMFPQFFCRFFFRCS,

SEQ ID NO: 9
CWFCRAFIKRFQAMIPKGERMLPQLVCRLVLRCS,

SEQ ID NO: 10
CWLCRALIKRIQAMIPKGERMFPQFFCRFFFRCS,

SEQ ID NO: 11
CWFCRAFIKRFQAMIPKGERMFPQFFCRFFFRCS,

SEQ ID NO: 12
CWLCRALIKRIQAMIPXGGRMLPQLVCRLVLRCS,

SEQ ID NO: 13
FPIPLPYCWLCRALIKRIQAMIPKGGRMLPQLVCRLVLRCS,

SEQ ID NO: 14
FPCPLPYCWLCRALIKRIQAMIPKGGRMLPQLVCRLVLRCS,

SEQ ID NO: 15
CPIPLPYCWLCRALIKRIQAMIPKGGRMLPQLVCRLVLRCS,

SEQ ID NO: 16
CWLCRALIKRIQAMIPKGALAVAVAQVCRVVPLVAGGICQALAERY
SVILLDTLLGRMLPQLVCRLVLRCS,

SEQ ID NO: 17
CWLCRALIKRIQAMIPKGALAVAVAQVCRVVPLVAGGICQFLAERY
SVILLDTLLGRMLPQLVCRLVLRCS,

SEQ ID NO: 18
FPIPLPYCWLCRALIKRIQAMIPKGALAVAVAQVCRVVPLVVGGI
CQYLAERYSVILLDTLLGRMLPQLVCRLVLRCS,

SEQ ID NO: 19
CPIPLPYCWLCRALIKRIQAMIPKGALAVAVAQVCRVVPLVVGGI
CQYLAERYSVILLDTLLGRMLPQLVCRLVLRCS,

```
                                                    SEQ ID NO: 20
FPCPLPYCWLCRALIKRIQAMIPKGALAVAVAQVCRVVPLVVGG
ICQYLAERYSVILLDTLLGRMLPQLVCRLVLRCS,

SEQ ID NO: 21
FGIPFFPVHLKRLLVVVVVVVLVVVVIVGALLMGL,

SEQ ID NO: 22
FGIPFFPVHLKRLLVPVVVVVLVVVVIVGALLMGL,

SEQ ID NO: 23
FGIPFFPVHLKRLLVVVVVPVLVVVVIVGALLMGL,

SEQ ID NO: 24
FGIPFFPVHLKRLLVVVVVVVLVPVVIVGALLMGL,

SEQ ID NO: 25
FGIPFFPVHLKRLLVVVVVVVLVVVVIPGALLMGL,

SEQ ID NO: 26
FKFKFKFKFKFKFKFKFKFKFK,

SEQ ID NO: 27
KFFFFKFFFFKFFFFKFFFFK,

SEQ ID NO: 28
FRFRFRFRFRFRFRFRFRFRFR,

SEQ ID NO: 29
RFFFFRFFFFRFFFFRFFFFR,

SEQ ID NO: 30
RFFFFKFFFFRFFFFRFFFFK,
``` and combinations thereof.

21. The lung surfactant composition according to claim 1 further comprising a therapeutic agent.

22. A method of treating endogenous surfactant dysfunctional lung tissue comprising:
providing a lung surfactant composition according to claim 1; and
administering the lung surfactant composition to a patient having lung tissue characterized by endogenous surfactant deficiency and/or dysfunction, wherein said administering is effective to coat alveolar surfaces of the affected lung tissue with the surfactant composition, thereby treating the surfactant deficient and/or dysfunctional lung tissue.

23. The method according to claim 22, wherein said administering is effective to prevent the onset or reduce the severity of respiratory deficit of neonatal respiratory distress syndrome, clinical acute lung injury (ALI) and/or acute respiratory distress syndrome (ARDS).

24. A method of delivering a therapeutic agent comprising:

introducing a therapeutic agent into a lung surfactant composition according to claim 1 under conditions effective to encapsulate the therapeutic agent in liposomal vesicles; and
administering the lung surfactant composition containing the therapeutic agent to a subject under conditions effective to deliver the therapeutic agent to lung tissue.

25. The lung surfactant composition of claim 1, wherein when $X_1$, $Y_1$, and $Y_2$ are each O, $R_1$ and $R_2$ are not both saturated C16 hydrocarbons of formulae (Ia) and (Ib).

26. The lung surfactant composition of claim 1, wherein when X, $Y_1$, and $Y_2$ are each O, $R_1$ and $R_2$ are not both saturated C14 hydrocarbons of formula (Ia), saturated C15 hydrocarbons of formula (Ia), saturated C16 hydrocarbons of formulae (Ia,b), saturated or monounsaturated C18 hydrocarbons of formulae (Ia,b), and $R_1$ is not a saturated C18 hydrocarbon when $R_2$ is a saturated C12 hydrocarbon of formula (Ib).

27. A lung surfactant composition comprising:
one or more lung surfactant proteins or surface active synthetic peptides;
a phospholipase-resistant phospho-choline compound; and
a phospholipase-resistant phospho-glycerol compound according to formulae (Ia) or (Ib)

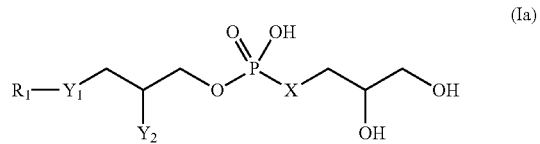

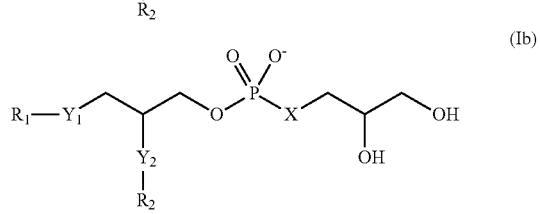

wherein,
X is O or $(CH_2)_n$ where n is an integer from 0 to 5,
$Y_1$ and $Y_2$ are independently O, S, or $SO_2$, and
$R_1$ and $R_2$ are independently C8-C24 hydrocarbons.

* * * * *

UNITED STATES PATENT AND TRADEMARK OFFICE
CERTIFICATE OF CORRECTION

Page 1 of 1

PATENT NO. : 9,447,127 B2
APPLICATION NO. : 14/030719
DATED : September 20, 2016
INVENTOR(S) : Notter et al.

It is certified that error appears in the above-identified patent and that said Letters Patent is hereby corrected as shown below:

In the Specification

At Column 1, Lines 12-14, please delete the following:
"grant numbers R01 HL-56176, RO1 HL-25170, RO1 HL-32242, KO4-HL-00945, P50 HL-36543, and RO1 HL-55534"
And insert in its place the following:
--HL056176, HL025170, HL032242, HL000945, HL036543, and HL055534--.

Signed and Sealed this
Fourteenth Day of November, 2017

Joseph Matal
*Performing the Functions and Duties of the
Under Secretary of Commerce for Intellectual Property and
Director of the United States Patent and Trademark Office*